US005801155A

United States Patent [19]
Kutyavin et al.

[11] Patent Number: 5,801,155
[45] Date of Patent: Sep. 1, 1998

[54] COVALENTLY LINKED OLIGONUCLEOTIDE MINOR GROVE BINDER CONJUGATES

[75] Inventors: Igor V. Kutyavin; Eugeny A. Lukhtanov, both of Bothell; Howard B. Gamper; Rich B. Meyer, Jr., both of Woodinville, all of Wash.

[73] Assignee: Epoch Pharmaceuticals, Inc., Bothell, Wash.

[21] Appl. No.: 415,370

[22] Filed: Apr. 3, 1995

[51] Int. Cl.[6] .......................... A01N 43/04; A01N 43/38; C07H 21/00; C07D 233/02
[52] U.S. Cl. ................... 514/44; 514/419; 536/25.3; 536/25.32; 546/270; 546/271; 548/311.1; 548/312.4
[58] Field of Search ................... 514/419, 44, 422, 514/383, 397, 343, 341, 340; 536/25.3, 25.32; 548/311.1, 312.4, 364.1; 546/270, 271

[56] References Cited

U.S. PATENT DOCUMENTS

| 4,835,263 | 5/1989 | Nguyen et al. ................ 536/27 |
| 5,237,101 | 8/1993 | Nicolaou et al. ............... 568/28 |
| 5,395,849 | 3/1995 | Wittman et al. ................ 514/419 |
| 5,446,137 | 8/1995 | Maag et al. ................... 536/23.1 |

FOREIGN PATENT DOCUMENTS

WO92/20698  11/1992  WIPO .................. C07H 21/04

OTHER PUBLICATIONS

Boder et al. Studies on the total synthesis of CC–1065: Preparation of a synthetic, simplified 3–carbamoyl–1, 2–dihydro–3H–pyrrolo[3,2–e]indole dimer/trimer/tetramer (CDPI dimer/trimer/tetramer) and development of methodology for PDE–I dimer methyl este, 1987.

Rao et al. "Synthesis of novel thiazole–containing DNA minor groove binding oligopeptides related to the antibiotic distamycin" J. Org. Chem., vol. 55, pp. 728–737, 1990.

Tabone et al. "Factors influencing the extent and regiospecificity of cross–linkk formation between single–stranded DNA and reactive complementary oligodeoxynucleotides" Biochemistry, vol. 33, pp. 375–383, 1994.

Webb, Thomas R. and Matteucci, Mark D. 1986 "Hybridization triggered cross–linking of deoxyoligonucleotides", Nucleic Acids Res., 14, 7661–7674.

Webb, T.R.; Matteucci, M.D. J. Am Chem. Soc., 1986, 108, 2764.

Kazimierczuk et al. J. Am. Chem. Soc., 1984, 106, 6379–6382.

Robins et al. Can. J. Chem., 60:554 (1982).
Robins et al. J. Org. Chem. 1983, 48:1854.
Sonveaux, Bioorganic Chemistry, 14:274–325 (1986).
Jones in "Oligonucleotide Synthesis, a Practical Approach", M.J. Gait, Ed., IRL Press, pp. 23–34 (1984).
Gibson, K.J., & Benkovic, S.J. (1987) Nucleic Acids Res., 15, 6455.
Boger, R.S. Coleman, and B.J. Invergo, J. Org. Chem., (1987), vol. 52, 1521–1530.
Grehn, L.V. Ragnarsson, J. Org. Chem., 1981, 46, 3492–3497.
Orum et al. Nucleic Acid Research, (1993) 21: 5332–5336.
Gamper, H.B. et al. Mucleic Acids Res., 1993 vol. 21 No. 1, 145–150.
M. Gait (ed.), Oligonucleotide Synthesis, A Practical Approach, IRL Press, 1984, Oxford, UK, pp. 35–81.

(List continued on next page.)

Primary Examiner—Ardin H. Marschel
Assistant Examiner—Jezia Riley
Attorney, Agent, or Firm—Klein & Szekeres, LLP

[57] ABSTRACT

Minor groove binding molecules are covalently bound to oligonucleotides which in their base sequence are complementary to a target sequence of single stranded or double stranded DNA, RNA or hybrids thereof. The covalently bound oligonucleotide minor groove binder conjugates strongly bind to the target sequence of the complementary strand.

28 Claims, 1 Drawing Sheet

Figure 1: Slot blot hybridization of unmodified ODN or 3'-ODN-CDPI, conjugates to M13mp19 (+) strand DNA. Underlined nucleotides represent mismatches with the targeted plasmid sequence.

OTHER PUBLICATIONS

Petrie, C.R. et al. *Bioconjugate Chemistry*, 1992, 3, 85–87.

Jost, J.-P., et al. (1989) "Quantitative presipitation of short oligonucleotides with low concentrations of cetyltrimethylammonium bromide" *Nucleic Acids Res.* 17, 2143.

Godovikov, T.S. et al. 1989. *Bioorgan. Khim*, 15, 1246–1259.

Lokhov, S.G. et al. 1992. *Bioconjugate Chem.* 3, 414.

Lee, et al., *Biochemistry*, 1994, 33: 6024–6030.

Larhammar, Dan et al. *Proc. Natl. Acad. Sci. USA* (1983) 80: 7313–7317.

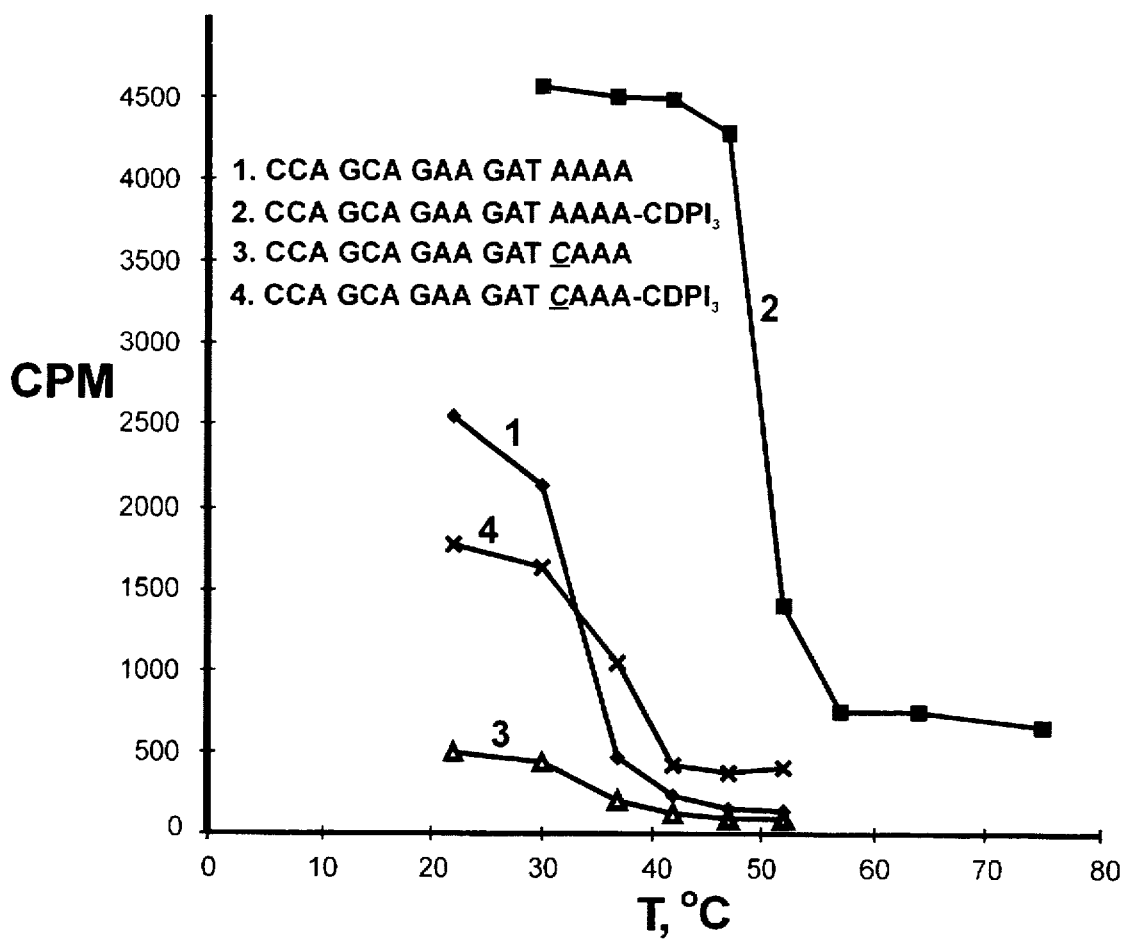
Figure 1: Slot blot hybridization of unmodified ODN or 3'-ODN-CDPI$_3$ conjugates to M13mp19 (+) strand DNA. Underlined nucleotides represent mismatches with the targeted plasmid sequence.

COVALENTLY LINKED OLIGONUCLEOTIDE MINOR GROVE BINDER CONJUGATES

FIELD OF THE INVENTION

The present invention is directed to new derivatives of oligonucleotides. More particularly, the present invention is directed to oligonucleotide derivatives wherein one or more minor groove binding molecules are covalently attached to the oligonucleotide. The oligonucleotide minor groove binding moiety conjugates show strong affinity to hybridize and strongly bind to complementary sequences of single or double stranded nucleic acids, and thereby have utility as sequence specific probes and as antisense and anti-gene therapeutic agents.

BRIEF DESCRIPTION OF THE PRIOR ART

Minor groove binding agents which non-covalently bind into the minor groove of double stranded DNA are known in the art. Intercalating agents which bind to double stranded DNA or RNA are also well known in the art. Intercalating agents are, generally speaking, flat aromatic molecules which non-covalently bind to double stranded DNA or RNA by positioning (intercalating) themselves between interfacing purine and pyrimidine bases of the two strands of double stranded DNA or RNA. U.S. Pat. No. 4,835,263 describes oligonucleotides which are covalently bound to an intercalating group. Such oligonucleotides carrying an intercalating group can be useful as hybridization probes.

SUMMARY OF THE INVENTION

The present invention relates to a covalently bound oligonucleotide and minor groove binder combination which includes an oligonucleotide having a plurality of nucleotide units, a 3'-end and a 5'-end, and a minor groove binder moiety covalently attached to at least one of said nucleotides. The minor groove binder is typically attached to the oligonucleotide through a linking group comprising a chain of no more than 15 atoms. The minor groove binder moiety is a radical of a molecule having a molecular weight of approximately 150 to approximately 2000 Daltons which molecule binds in a non-intercalating manner into the minor groove of double stranded DNA, RNA or hybrids thereof with an association constant greater than approximately $10^3 M^{-1}$.

In another aspect, the present invention relates to the process of synthesizing certain covalently bound oligonucleotide minor groove binder combinations, and to the manner of using such combinations for hybridization probe and related analytical and diagnostic, as well as therapeutic (anti-sense and anti-gene) purposes.

BRIEF DESCRIPTION OF THE DRAWINGS

FIG. 1 is a graph showing the results of a slot blot hybridization assay.

DETAILED DESCRIPTION OF THE INVENTION GENERAL EMBODIMENTS

A prominent feature of the novel composition of matter of the present invention is that a minor groove binding molecule is covalently bound to an oligoneucleotide. As is noted in the introductory section of the present application for patent, a minor groove binder is a molecule that binds within the minor groove of double stranded deoxyribonucleic acid (DNA). Although a general chemical formula for all known minor groove binding compounds cannot be provided because such compounds have widely varying chemical structures, compounds which are capable of binding in the minor groove of DNA, generally speaking, have a crescent shape three dimensional structure. Most minor groove binding compounds of the prior art have a strong preference for A-T (adenine and thymine) rich regions of the B form of double stranded DNA. The minor groove binding compounds, or more accurately stated moieties of the oligonucleotide-minor groove binding conjugates of the present invention, also have the same preference. (The oligonucleotide-minor groove binding conjugates of the present invention are hereinafter sometimes referred to as ODN-MGB.) Nevertheless, minor groove binding compounds which would show preference to C-G (cytosine and guanine) rich regions are also theoretically possible. Therefore, ODN-MGB compounds incorporating a radical or moiety derived from minor groove binder molecules having preference for C-G regions are also within the scope of the present invention. The preference for A-T regions of the known minor groove binders is currently explained by the existence of an unfavorable steric interference between the 2-amino group of guanine and some well known minor groove binders. However, as it will become apparent from the ensuing further description, when guanine is replaced by hypoxanthine in an ODN-MGB of the present invention, the potential for the above-noted unfavorable steric interference no longer exists and strong binding of the ODN-MGB to a complementary strand may occur.

Generally speaking, minor groove binding compounds known in the prior art do not bind to double stranded RNA or to a double stranded hybrid of DNA and RNA. However, the ODN-MGB compounds of the present invention exhibit potential for binding to single stranded RNA, and the foregoing feature forms another interesting and novel aspect of the present invention.

Examples of known minor groove binding compounds of the prior art, which can, in accordance with the present invention, be covalently bound to ODNs to form the novel ODM-MGB conjugates are certain naturally occurring compounds such as netropsin, distamycin and lexitropsin, mithramycin, chromomycin $A_3$, olivomycin, anthramycin, sibiromycin, as well as further related antibiotics and synthetic derivatives. Certain bisquarternary ammonium heterocyclic compounds, diarylamidines such as pentamidine, stilbamidine and berenil, CC-1065 and related pyrroloindole and indole polypeptides, Hoechst 33258, 4'-6-diamidino-2-phenylindole (DAPI) as well as a number of oligopeptides consisting of naturally occurring or synthetic amino acids are minor groove binder compounds. The chemical structures of the following examples are illustrated below.

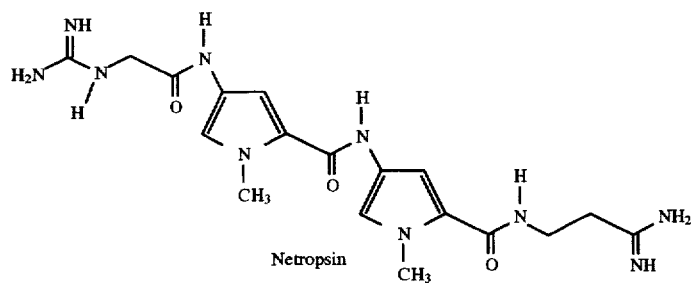
Netropsin
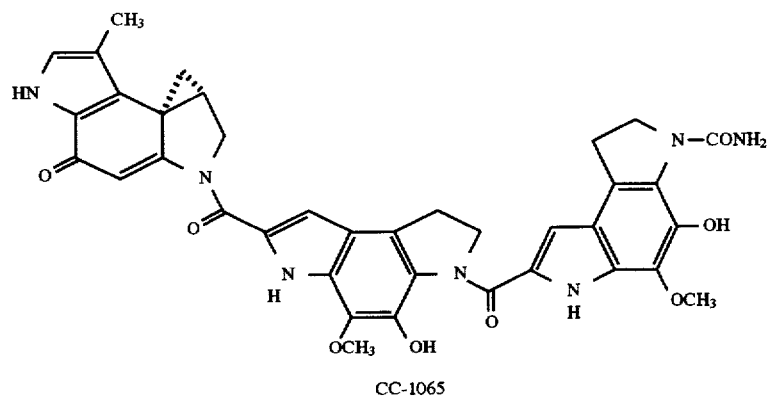
CC-1065
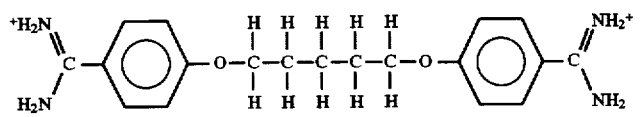
Pentamidine
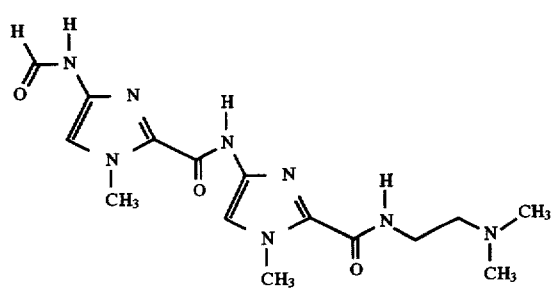
Lexitropsin
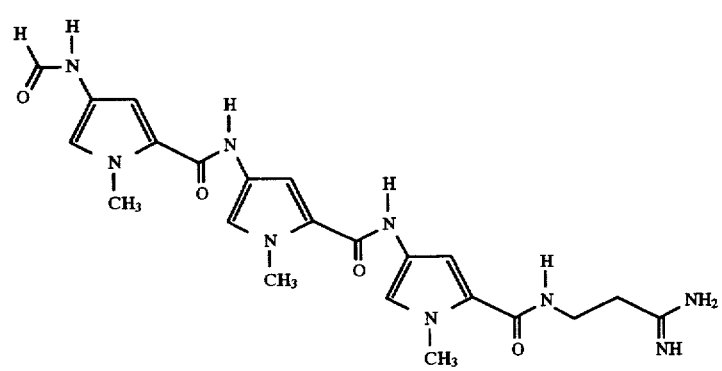
Distamycin -continued
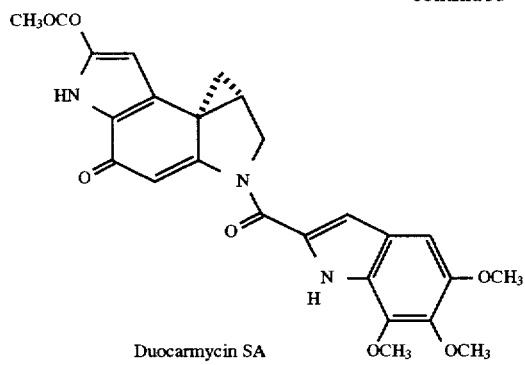
Duocarmycin SA
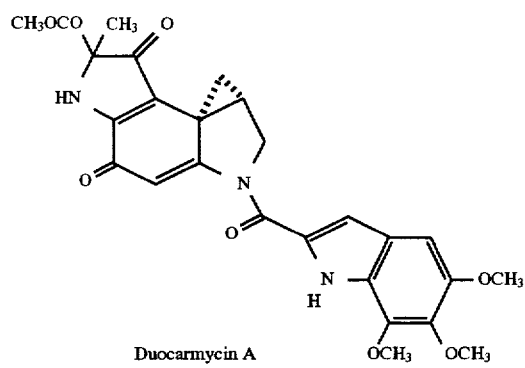
Duocarmycin A
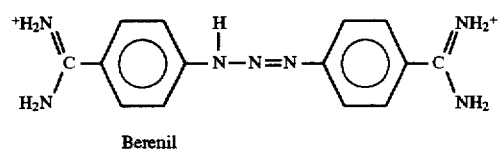
Berenil
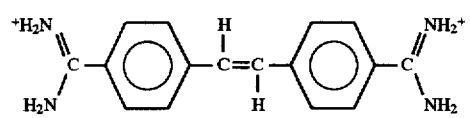
Stilbamidine
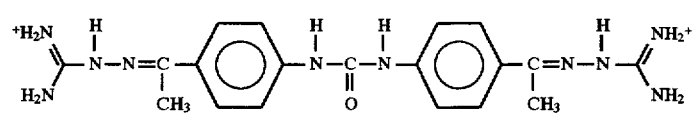
DDUG
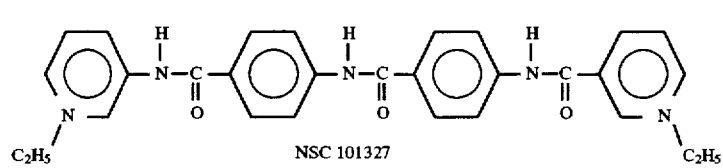
NSC 101327
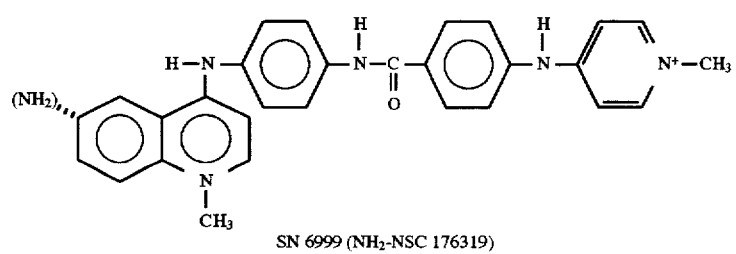
SN 6999 ($NH_2$-NSC 176319)

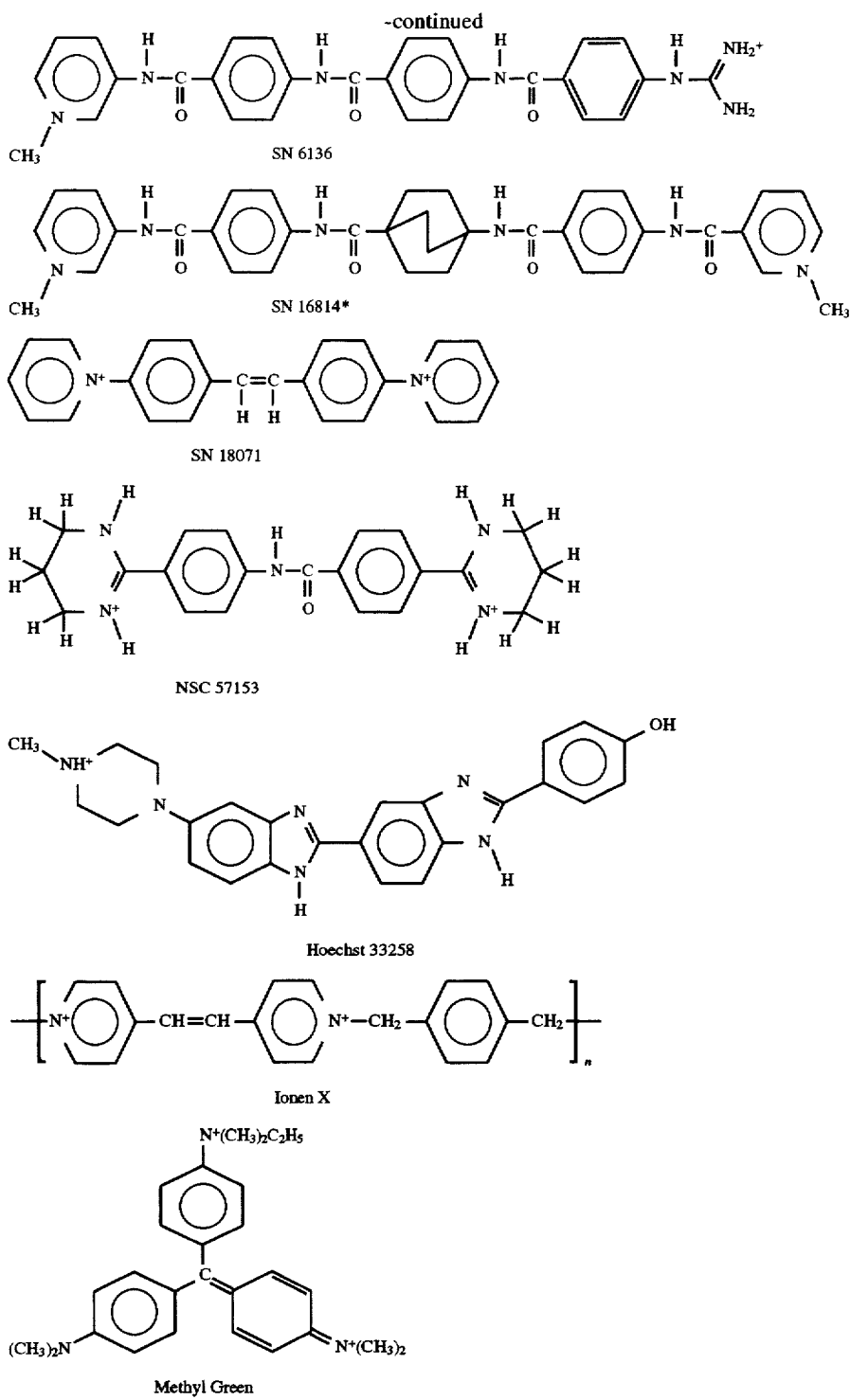

For the purposes of the present invention a molecule is a minor groove binder if it is capable of binding within the minor groove of double stranded DNA with an association constant of $10^3 M^{-1}$ or greater. This type of binding can be detected by well established spectrophotometric methods, such as ultraviolet (u.v.) and nuclear magnetic resonance (nmr) spectroscopy and also by gel electrophoresis. Shifts in u.v. spectra upon binding of a minor groove binder molecule, and nmr spectroscopy utilizing the "Nuclear Overhauser" (NOSEY) effect are particularly well known and useful techniques for this purpose. Gel electrophoresis detects binding of a minor groove binder to double stranded DNA or fragment thereof, because upon such binding the mobility of the double stranded DNA changes.

Intercalating molecules or agents are readily distinguished from minor groove binders on the basis that the intercalating agents are flat aromatic (preferably polycyclic) molecules versus the "crescent shape" or analogous geometry of the minor groove binders. An experimental distinction can also be made by nmr spectroscopy utilizing the Nuclear Overhauser effect.

As noted above, for the purposes of the present invention a molecule is a minor groove binder if its association constant within the minor groove of double stranded DNA is $10^3 M^{-1}$ or greater. However, some minor groove binders bind to the high affinity sites of double stranded DNA with an association constant of the magnitude of $10^7$ to $10^9 M^{-1}$.

In accordance with the present invention, the minor groove binder molecule is derivatized, in essence formed into a "radical" and linked to an appropriate covalent structure or chain of atoms that attaches the minor groove binder to the ODN. In a sense, the linking "chain" can and sometimes is considered as part of the minor groove binder since the nature of the linkage is such that it does not adversely affect the minor groove binding properties of the ODN-MGB molecule. However, it suits the present description better to conceptually separate the minor groove binder from the group that covalently attaches it to the ODN. The radical "formed" from the minor group binder molecule is hereinafter referred to as the "minor groove binder moiety", and the covalent linkage (which may be a chain of up to approximately 15 atoms) that attaches the minor groove binder moiety to the oligonucleotide is called the "linking group". The preferred embodiments of the minor groove moieties in accordance with the present invention are described in detail after description of the oligonucleotide portion of the ODN-MGB conjugate compounds of the present invention.

Broadly speaking, the oligonucleotide portion of the ODN-MGB conjugates of the present invention comprise approximately 3 to 100 nucleotide units. The nucleotide units which can be incorporated into the ODNs in accordance with the present invention include the major heterocyclic bases naturally found in nucleic acids (uracil, cytosine, thymine, adenine and guanine) as well as naturally occurring and synthetic modifications and analogs of these bases such as hypoxanthine, 2-aminoadenine, 2-thiouracil, 2-thiothymine, 5-$N^4$ ethenocytosine, 4-aminopyrrazolo[3,4-d]pyrimidine and 6-amino-4-hydroxy-[3,4-d]pyrimidine. The respective structures of the 2-deoxyribosides of 5-$N^4$ ethenocytosine 4-aminopyrrazolo[3,4-d]pyrimidine and of 6-amino-4-hydroxy-[3,4-d]pyrimidine are shown below.

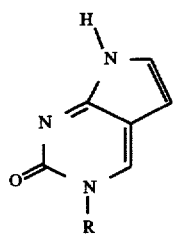

5-$N^4$ ethenocytosine
2-deoxyriboside

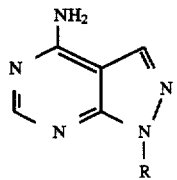

4-aminopyrazolo[3,4-d]pyrimidine
2-deoxyriboside

-continued

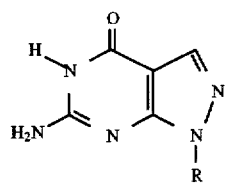

6-amino-4-hydroxypyrazole-[3,4-d]pyrimidine
2-deoxyriboside
R = 2-deoxy-β-D-ribofuranosyl In addition, the nucleotide units which are incorporated into the ODNs of the ODN-MGB conjugates of the present invention may have a cross-linking function (an alkylating agent) covalently bound to one or more of the bases, through a linking arm. Since the ODN-MGB conjugates having an attached cross-linking agent form an important class of preferred embodiments of the present invention these structures will be described in more detail below.

The "sugar" or glycoside portion of the ODN-MGBs of the present invention may comprise deoxyribose, ribose, 2-fluororibose, 2-O alkyl or alkenylribose where the alkyl group may have 1 to 6 carbons and the alkenyl group 2 to 6 carbons. In the naturally occurring nucleotides and in the herein described modifications and analogs the deoxyribose or ribose moiety forms a furanose ring, the glycosydic linkage is of the β configuration and the purine bases are attached to the sugar moiety via the 9-position, the pyrimidines via the 1-position and the pyrazolopyrimidines via the 1-position. Presently, oligodeoxyribonucleotides are preferred in accordance with the present invention, therefore the preferred sugar is 2-deoxyribose. The nucleotide units of the ODN's are interconnected by a "phosphate" backbone, as is well known in the art. The ODNs of the ODN-MGB conjugates of the present invention may include, in addition to the "natural" phosphodiester linkages, phosphorothiotes and methylphosphonates.

The ODNs of the ODN-MGB conjugates of the present invention may also have a relatively low molecular weight "tail moiety" attached to either at the 3' or 5'-end. The "tail moiety" in this particular context is to be distinguished from the minor groove binding moiety, which is preferably also attached to the 3' or 5' ends, or to both. Thus, in this context the "tail moiety" if present at all, is attached to the end of the ODN which does not bear the minor groove binder moiety. By way of example, a tail molecule may be a phosphate, a phosphate ester, an alkyl group, and aminoalkyl group, or a lipophilic group.

With regard to the possible variations of the nucleotide units, the "phosphate backbone" and "tail" of the ODNs of the ODN-MGB conjugates of the present invention, the following should be kept in mind. The principal useful action of the ODN-MGB conjugates of the present invention lies in the ability of the ODN portion of the molecule to bind to a complementary sequence in single stranded DNA, RNA, double stranded DNA, and DNA-RNA hybrid, in a manner in which the minor groove binding moiety is incorporated in the newly formed "duplex" and thereby strengthens the bond, that is, increases the melting temperature (and association constant) of the newly formed duplex. Additionally, those preferred embodiments of the ODN-MGB conjugates of the present invention which include a cross-linking agent, also result in permanent covalent attachment of the ODN-MGB molecule to the complementary DNA or RNA strand, resulting in a permanently bound form. In light of the foregoing, those skilled in the art will readily understand that the primary structural limitation of the various component parts of the ODN portion of the ODB-MGB conjugate of the present invention lies only in the ability of the ODN portion to form a complementary strand to any specific target sequence, and that a large number of structural modifications, per se known in the art, are possible within these bounds. Moreover, synthetic methods for preparing the various heterocyclic bases, nucleosides, nucleotides and oligonucleotides which can form the ODN portion of the ODN-MGB conjugates of the present invention, are generally speaking well developed and known in the art. $N_4,N_4$-ethano-5-methyldeoxycytidine, its nucleoside, nucleotide and/or oligonucleotides incorporating this base can be made in accordance with the teachings of Webb, T. R.; Matteucci, M. D. *Nucleic Acids Res.*, 1986, 14, 7661–7674, Webb, T. R.; Matteucci, M. D. *J. Am. Chem. Soc.*, 1986, 108, 2764. 4-aminopyrazolo[3,4-d]pyrimidine, 6-amino-4-hydroxypyrazolo[3,4-d]pyrimidine, their nucleosides, nucleotides and oligonucleotides incorporating this base can be made in accordance with the teachings of Kazimierczuk et al. *J. Am. Chem. Soc.*, 1984, 106, 6379–6382. Whereas oligonucleotide synthesis, in order to prepare an ODN of specific predetermined sequence so as to be complementary to a target sequence, can be conducted in accordance with the state of the art, a preferred method is described below. The preferred method incorporates the teaching of application Ser. No. 08/090,408 filed on Jul. 12, 1993, which has been allowed and the issue fee was paid. The specification of application Ser. No. 08/090,408 is hereby expressly incorporated by reference.

The linking group is a moiety which covalently links the ODN portion of the conjugate to the minor groove binder moiety. Preferably, the linking group is such that the linkage occurs through a chain of no more than 15 atoms. Also preferably in accordance with the present invention the minor groove binder moiety is covalently attached to either the 3' or 5' end of the oligonucleotide. Nevertheless, attachment to a nucleotide in intermediate position, and particularly to the heterocyclic base of the nucleotide in intermediate position is also within the scope of the invention. Generally speaking, the linking group is derived from a bifunctional molecule so that one functionality such as an amine functionality is attached for example to the phosphate on the 5' end of the ODN, and the other functionality such as a carbonyl group (CO) is attached to an amino group of the minor groove binder moiety. Alternatively, the linking group may be derived from an amino alcohol so that the alcohol function is linked, for example, to the 3'-phosphate end of the ODN and the amino function is linked to a carbonyl group of the minor groove binder moiety. Still another alternative of a linking group includes an aminoalcohol (attached to the 3'-phosphate with an ester linkage) linked to an aminocarboxylic acid which in turn is linked in a peptide bond to the carbonyl group of the minor groove binder. Thus, preferred embodiments of the linking group have the formulas $—HN(CH_2)_mCO$, $O(CH_2)_mCO$ and $(CH_2)_mCH(OH)(CH_2)_mNHCO(CH_2)_mNH$ where the limitation on m is that the minor groove binder moiety should not be separated by more than approximately 15 atoms from the ODN. Preferred embodiments of linking groups are $—O(CH_2)_6NH$, $—OCH_2CH(OH)CH_2NHCOCH_2CH_2NH$ and $—HN(CH_2)_5CO$. As it was noted above, the linking group could also be conceptualized as part of the minor groove binder moiety, which in that case would be considered directly attached to the ODN.

The basic limitation for the minor groove binder moiety has been set forth above, and is not definable by specific chemical structure. In addition to the molecular structure which causes minor groove binding, the minor groove binder moiety may also carry additional functions, as long as those functions do not interfere with minor groove binding ability. For example a reporter group, which makes the minor groove binder readily detectable by color, uv, spectrum or other readily discernible physical or chemical characteristic, may be covalently attached to the minor groove binder moiety. An example for such a reporter group is a diazobenzene function which in the example of a preferred embodiment is attached to a carbonyl function of the minor groove binder through a $—HN(CH_2)_mCOO(CH_2)_mS(CH_2)_m—$ bridge. Again, the reporter group or other like function carried by the minor groove binder can also be conceptualized as part of the minor groove binder moiety itself.

Preferred embodiments of the ODN-MGB conjugates are defined by the following chemical Formula 1. This definition includes the preferred embodiments of the minor groove binder moiety in accordance with the present invention, which may also include all or part of the linking group and other appendant groups such as a reporter group, as discussed above:

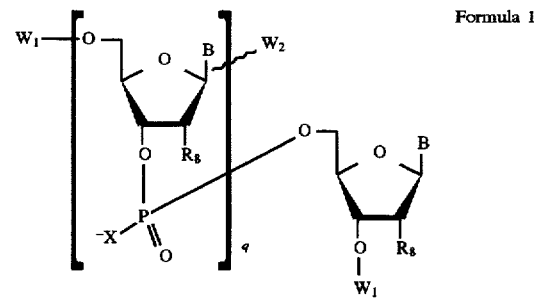

Formula 1 where x is O or S;

q is an integer between 3 to 100;

$R_8$ is H, OH, alkoxy having 1 to 6 carbons, $O—C_2–C_6$alkenyl, or F;

B is an aglycon selected from a group consisting of a heterocyclic base naturally found in nucleic acids and hypoxanthine, 2-aminoadenine, 2-thiouracil, 2-thiothymine, 5-$\underline{N}^4$-ethenocytosine, 4-aminopyrrazolo [3,4-d]pyrimidine, 6-amino-4-hydroxy-[3,4-d]pyrimidine;

$W_1$ is H, $PO(OH)_2$ or a salt thereof, or a minor groove binder moiety attached to the 3' or 5' end of said oligonucleotide, the $W_1$ group including the linking group which covalently binds the minor groove binder moiety to the oligonucleotide through no more than 15 atoms.;

$W_2$ is absent or is a minor groove binder moiety attached to one of the aglycons B, the $W_2$ group including the linking group which covalently binds the minor groove binder moiety to said aglycon, or $W_2$ is a cross-linking functionality including a linker arm which covalently binds the cross-linking functionality to said aglycon, wherein the minor groove binder moiety is a radical of a molecule having a molecular weight of approximately 150 to approximately 2000 Daltons that bind in a non-intercalating manner into the minor groove of double stranded DNA, RNA or hybrids thereof with an association constant greater than approximately $M^{-1}$ with the proviso that at least one of said $W_1$ and $W_2$ groups is a minor groove binder moiety; and wherein further the minor groove binder moiety including the linking group has the formula selected from the group consisting of groups (a), (b), (c), (d) and (e):

  (a)

where $Y_1$ represents a 5-membered ring having two double bonds and 0 to 3 heteroatoms selected from the group consisting of N, S and O, the NH and CO groups are attached respectively to two ring carbons which are separated by one ring atom from one another, the ring atom positioned between said two ring carbons is substituted only with H or is unsubstituted, each of the remaining ring atoms may be optionally substituted with 1, 2 or 3 $R_3$ groups;

  (b)

where $Y_2$ is a ring system consisting of a 6-membered aromatic ring condensed with a 5-membered ring having one double bond, the condensed ring system having 0 to 3 heteroatoms selected from the group consisting of N, S and O, each of the $R_6N$ and CO groups is attached to a ring carbon which is in a different ring of the condensed ring system, and which is the second ring atom, respectively, from one common bridge-head ring atom, the CO and $NR_6$ groups thereby positioning 2 non-bridgehead ring atoms between themselves on one side and 3 non-bridgehead ring atoms on the other side of the condensed ring system, the two non-bridgehead ring atoms on the one side being optionally substituted with an $R_7$ group, the three non-bridgehead ring atoms on the other side of the condensed ring system being optionally substituted with an $R_3$ group;

  (c)

where $Y_3$ is a 6-membered aromatic ring having 0 to 3N heteroatoms, and where each of the CO and NH groups is attached to a ring carbon, said ring carbons being in 1,4 position relative to one another, two ring atoms not occupied by the CO or NH groups on either one of the two sides of the 6-membered ring being optionally substituted with an $R_3$ group, the two ring atoms not occupied on the other side of the 6 membered ring being optionally substituted with an $R_7$ group;

  (d)

where $Y_4$ is a 6-membered aromatic ring having 0 to 3N heteroatoms, and where each of the CO and NH groups is attached to a ring carbon, said ring carbons being in 1,4 position relative to one another in each ring, two ring atoms not occupied by the CO or NH groups on either one of the two sides of the 6-membered ring being optionally substituted with an $R_3$ group, the two ring atoms not occupied on the other side of the 6 membered ring being optionally substituted with an $R_7$ group;

  (e)

where $Y_5$ is a ring system consisting of a 6-membered aromatic ring condensed with a 5-membered ring having one double bond, the condensed ring system having 0 to 3 heteroatoms selected from the group consisting of N, S and O, each of the $R_1$ and $R_2$ groups is attached to a ring carbon which is in a different ring of the condensed ring system, and which is the second ring atom, respectively, from one common bridge-head ring atom, the $R_1$ and $R_2$ groups thereby positioning 2 non-bridgehead ring atoms between themselves on one side and 3 non-bridgehead ring atoms on the other side of the condensed ring system, the two non-bridgehead ring atoms on the one side being optionally substituted with an $R_7$ group, the three non-bridgehead ring atoms on the other side of the condensed ring system being optionally substituted with an $R_3$ group;

where $R_1$ and $R_2$ independently are H, F, Cl, Br, I, $NH_2$, $NHR_4$, $N(R_4)_2$, $N(R_4)_3^+$, OH, —O—, —S—, $OR_4$, SH, $SR_4$, $COR_4$, $CONHR_4$, $CON(R_4)_2$, $R_4$, $H_2N(CH_2)_mCO$, $CONH_2$, $CONHR_4$, $H_2N(CH_2)_mCOO(CH_2)_mS(CH_2)_m$ $C_6H_4NNC_6H_4$, —$HN(CH_2)_mCO$, —CONH—, —$CONR_4$, —$HN(CH_2)_mCOO(CH_2)_mS(CH_2)_m$ $C_6H_4NNC_6H_4$, and —$(CH_2)_mCH(OH)(CH_2)_mNHCO$ $(CH_2)_mNH$—, or one of the $R_1$ and $R_2$ groups is absent;

$R_3$ is selected from the group consisting of F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$ and $R_4$, or the $R_3$ groups may form a 3, 4, 5 or 6 membered ring condensed to the $Y_1$ ring;

$R_4$ is an alkyl or cycloalkyl group having 1 to 20 carbons, an alkenyl or cycloalkenyl group having 1 to 20 carbons and 1 to 3 double bonds, a carbocyclic aromatic group of no more than 25 carbons, a heterocyclic aromatic group of no more than 25 carbons, a carbocyclic or heterocyclic arylalkyl group of no more than 25 carbons, where $R_4$ may be optionally substituted with 1, 2 or 3 F, Cl, Br, I, $NH_2$, $NHR_5$, $N(R_5)_2$, $N(R_5)_3^+$, OH, $OR_5$, SH, $SR_5$, $COR_5$, $CONHR_5$, $CON(R_5)_2$ or $R_5$ groups;

$R_5$ is alkyl of 1 to 6 carbons, $R_6$ is H, alkyl of 1 to 5 carbons, or $R_6$ and $R_7$ jointly form a 4, 5, or 6 membered ring, optionally an —O—, —S—, —NH—, —$NCH_3$—, or $\underline{N}$-lower alkyl group being part of said ring;

$R_7$ is F, methyl or ethyl; —$CH_2$—, or —$CH_2CH_2$—;

m is an integer between 1 to 10;

n is an integer between 1 to 10, and p is an integer between 1 to 5.

Still more preferred embodiments of the ODN-MBG conjugates of the present invention are those where the minor groove binder moiety is defined as follows:

(1) the minor groove binding moiety is represented by formula (a) above and the five membered ring has the structure

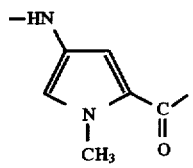

Formula 2

(2) the minor groove binding moiety is represented by formula (a) above wherein the five membered ring has the structure

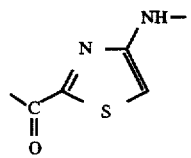

Formula 3 and (3) the minor groove binding moiety is represented by formula (b) and the condensed ring system has the structure

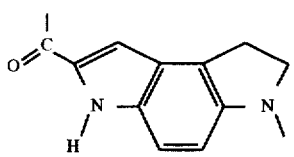

Formula 4

Embodiments containing a cross-linking functionality

A class of preferred embodiments of the ODN-MGB conjugates of the present invention also include one or more cross-linking functionalities whereby after the ODN-MGB conjugate is bound to a complementary target sequence of DNA, RNA or fragment thereof, the cross-linking functionality irreversibly reacts with the target and forms a covalent bond therewith. Advantages of such covalent linking to a target sequence are in analytical, diagnostic use, as in hybridization probes, and in therapeutic (anti-sense and anti-gene) applications. The minor groove binder moiety which is also covalently bound to the ODN that complements the target sequence, enhances the initial non-covalent binding of the ODN-MGB conjugate to the target sequence and therefore facilitates the subsequent covalent bonding through the cross-linking function. The following considerations are pertinent as far as the cross-linking functionalities or agents incorporated into this class of ODN-MGB conjugates are concerned.

The cross-linking agents incorporated in the present invention are covalently bonded to a site on the ODN-MGB. Its length and steric orientation should be such that it can reach a suitable reaction site in the target DNA or RNA sequence after the ODN-MGB is hybridized with the target. By definition, the cross-linking functionality or agent has a reactive group which will react with a reactive group of the target DNA or RNA sequence. The cross-linking agent (or agents) may be covalently attached to one or more of the heterocyclic bases, to the sugar or modified sugar residues, or to the phosphate or modified phosphate functions of the ODN-MGB conjugates. The cross-linking agent may also be attached to the minor groove binder moiety as long as it does not interfere with its minor groove binding ability. Preferably the cross-linking agent or functionality is attached to one of the heterocyclic bases.

In simple terms the cross-linking agent itself may conceptually be divided into two groups or moieties, namely the reactive group, which is typically and preferably an electrophilic leaving group (L), and an "arm" (A) which attaches the leaving group L to the respective site on the ODN-MGB. The leaving group L may be chosen from, for example, such groups as chloro, bromo, iodo, $SO_2R'''$, or $S^+R'''R''''$, where each of $R'''$ and $R''''$ is independently $C_{1-6}$alkyl or aryl or $R'''$ and $R''''$ together form a $C_{1-6}$alkylene bridge. Chloro, bromo and iodo are preferred. Within these groups haloacetyl groups such as —$COCH_2I$, and bifunctional "nitrogen mustards", such as —N—[$(CH_2)_2$—Cl]$_2$ are preferred. The leaving group will be altered by its leaving ability. Depending on the nature and reactivity of the particular leaving group, the group to be used is chosen in each case to give the desired specificity of the irreversibly binding probes.

Although as noted above the "arm" (or linker arm) A may conceptually be regarded as a single entity which covalently bonds the ODN-MGB to the leaving group L, and maintains the leaving group L at a desired distance and steric position relative to the ODN-MGB, in practice the "arm" A may be constructed in a synthetic scheme where a bifunctional molecule is covalently linked to the ODN-MGB, or to the ODN before the minor groove binder moiety is attached (for example by a phosphate ester bond to the 3' or 5' terminus, by a carbon-to-carbon bond to a heterocyclic base or by carbon to nitrogen bond to an amino substituted heterocyclic base) through its first functionality, and is also covalently linked through its second functionality (for example an amine) to a "hydrocarbyl bridge" (alkyl bridge, alkylaryl bridge or aryl bridge, or the like) which, in turn, carries the leaving group L.

A general formula of the cross linking function is thus —A—L, or —A—$L_2$ where L is the above defined leaving group and A is a moiety that is covalently linked to the ODN-MGB. The A "arm" moiety itself should be unreactive (other than through the leaving group L) under the conditions of hybridization of the ODN-MGB with the target sequence, and should maintain the leaving group L in a desired steric position and distance from the desired site of reactions such as an N-7 position of a guanosine residue in the target sequence. Generally speaking, the length of the A group should be equivalent to the length of a normal alkyl chain of approximately 2 to 20 carbons.

An examplary more specific formula for a class of preferred embodiments of the cross-linking function is

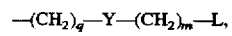

where L is the leaving group, defined above, each of m and q is independently 0 to 8, inclusive, and where Y is defined as a "functional linking group". For clarity of description this "functional linking group" is to be distinguished from the "linking group" that attaches the minor groove binder moiety to the ODN, although the functional linking groups described here for attaching the cross-linking agent can also be used for attaching a minor groove binder moiety to either end of the ODN, or to a nucleotide in intermediate position of the ODN. A "functional linking group" is a group that has two functionalities, for example —$NH_2$ and —OH, or —COOH and —OH, or —COOH and —$NH_2$, which are capable of linking the $(CH_2)_q$ and $(CH_2)_m$ bridges. An acetylenic terminus (HC≡C—) is also a suitable functionality for Y, because it can be coupled to certain heterocycles, as described below.

Other examplary and more specific formulas for a class of preferred embodiments of the cross-linking function are

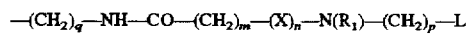

and

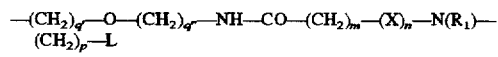

where q, m and L are defined as above in connection with the description of the cross-linking functions, q' is 3 to 7 inclusive, q" is 1 to 7 inclusive, X is phenyl or simple substituted phenyl (such as chloro, bromo, lower alkyl or lower alkoxy substituted phenyl), n is 0 or 1, p is an integer from 1 to 6, and $R_1$ is H, lower alkyl or $(CH_2)_p$—L. Preferably p is 2. Those skilled in the art will recognize that the structure —N($R_1$)—$(CH_2)_2$—L describes a "nitrogen mustard", which is a class of potent alkylating agents. Particularly preferred are within this class of ODN-MGB conjugates those where the cross-linking agent includes the functionality —N($R_1$)—$(CH_2)_2$—L where L is halogen, preferably chlorine; and even more preferred are those ODN-MGB conjugates where the cross linking agent includes the grouping —N—[$(CH_2)_2$—L]$_2$ (a "bifunctional" N-mustard).

A particularly preferred partial structure of the cross linking agent includes the grouping —CO—(CH₂)₃—C₆H₄—N—[(CH₂)₂Cl]₂.

In a preferred embodiment the just-noted cross-linking group is attached to an n-hexylamine bearing tail at the 5' and 3' ends of the ODN in accordance with the following structure:

R'—O—(CH₂)₆—NH—CO—(CH₂)₃—C₆H₄—N—[(CH₂)₂Cl]₂ where R' signifies the terminal 5'or 3'-phosphate group of the ODN. The other terminal, or a nucleotide in an intermediate position bears the minor groove binder moiety.

In accordance with other preferred embodiments, the cross-linking functionality is covalently linked to the heterocyclic base, for example to the uracil moiety of a 2'-deoxyuridylic acid building block of the ODN-MGB conjugate. The linkage can occur through the intermediacy of an amino group, that is, the "arm-leaving group combination" (A-L) may be attached to a 5-amino-2'-deoxyuridylic acid building unit of the ODN. In still other preferred embodiments the "arm-leaving group combination" (A-L) is attached to the 5-position of the 2'-deoxyuridylic acid building unit of the ODN by a carbon-to-carbon bond. Generally speaking, 5-substituted-2'-deoxyuridines can be obtained by an adaptation of the general procedure of Robins et al. (Can. J. Chem., 60:554 (1982); J. Org. Chem., 48:1854 (1983)). In accordance with this adaptation, palladium-mediated coupling of a substituted 1-alkyne to 5-iodo-2'-deoxyuridine gives an acetylene-coupled product. The acetylenic dUrd analog is reduced, with Raney nickel for example, to give the saturated compound, which is then used for direct conversion to a reagent for use on an automated DNA synthesizer. Examples of reagents which can be coupled to 5-iodo-2'-deoxyuridine in accordance with this method are HC≡CCH₂OCH₂CH₂N(CO)₂C₆H₄ (phtalimidoethoxypropyne) and HC≡CCH₂OCH₂CH₂NHCOCF₃ (trifluoroacetamidoethoxypropyne).

In these examples the nucleosides which are obtained in this scheme are incorporated into the desired ODN, and the alkylating portion of the cross-linking agent is attached to the terminal amino group only after removal of the respective phtalic or trifluoroacetyl blocking groups. Other examples of nucleotides where the crosslinking agent is attached to a heterocyclic base, are 2'-deoxy-4-aminopyrazolo[3,4-d]pyrimidine derivatives. These compounds can be made in accordance with the teaching of published PCT application WO: 90/03370 (published on Apr. 5, 1990).

Discussing still in general terms the structures of the modified ODNs of the present invention, it is noted that examination of double-stranded DNA by ball-and-stick models and high resolution computer graphics indicates that the 7-position of the purines and the 5-position of the pyrimidines lie in the major groove of the B-form duplex of double-stranded nucleic acids. These positions can be substituted with side chains of considerable bulk without interfering with the hybridization properties of the bases. These side arms may be introduced either by derivatization of dThd or dCyd, or by straightforward total synthesis of the heterocyclic base, followed by glycosylation. These modified nucleosides may be converted into the appropriate activated nucleotides for incorporation into oligonucleotides with an automated DNA synthesizer. With the pyrazolo[3,4-d]pyrimidines, which are analogs of adenine, the crosslinking arm is attached at the 3-position, which is equivalent to the 7-position of purine.

The crosslinking side chain (arm=A) should be of sufficient length to reach across the major groove from a purine 7- or 8-position, pyrimidine 5-position, pyrrolopyrimidine 5-position or pyrazolopyrimidine 3-position and reacting with the N-7 of a purine (preferably guanine) located above (on the oligomer 3'-side) the base pair containing the modified analog. The crosslinking side chain (arm=A) holds the functional group away from the base when the base is paired with another within the double-stranded complex. As noted above, broadly the arm A should be equivalent in length to a normal alkyl chain of 2 to 20 carbons. Preferably, the arms include alkylene groups of 1 to 12 carbon atoms, alkenylene groups of 2 to 12 carbon atoms and 1 or 2 olefinic bonds, alkynylene groups of 2 to 12 carbon atoms and 1 or 2 acetylenic bonds, or such groups substituted at a terminal point with nucleophilic groups such as oxy, thio, amino or chemically blocked derivatives thereof (e.g., trifluoroacetamido, phthalimido, CONR', NR'CO, and SO₂NR', where R'=H or C₁₋₆alkyl). Such functionalities, including aliphatic or aromatic amines, exhibit nucleophilic properties and are capable of serving as a point of attachment to such groups as —(CH₂)ₘ—L, and —CO—(CH₂)ₘ—(X)ₙ—N(R₁)—(CH₂)ₚ—L which are described above as components of examplary cross-linking functional groups.

After the nucleoside or nucleotide unit which carries the crosslinking functionality A-L, or a suitable precursor thereof, (such as the —(CH₂)_q—NH₂ or —(CH₂)_q—Y group, where Y terminates with a nucleophilic group such as NH₂) is prepared, further preparation of the modified oligonucleotides of the present invention can proceed in accordance with state-of-the-art. Thus, to prepare oligonucleotides, protective groups are introduced onto the nucleosides or nucleotides and the compounds are activated for use in the synthesis of oligonucleotides. The conversion to protected, activated forms may follow the procedures as described for 2'-deoxynucleosides in detail in several reviews. See, Sonveaux, Bioorganic Chemistry, 14:274-325 (1986); Jones, in "Oligonucleotide Synthesis, a Practical Approach", M. J. Gait, Ed., IRL Press, p. 23-34 (1984).

The activated nucleotides are incorporated into oligonucleotides in a manner analogous to that for DNA and RNA nucleotides, in that the correct nucleotides will be sequentially linked to form a chain of nucleotides which is complementary to a sequence of nucleotides in target DNA or RNA. The nucleotides may be incorporated either enzymatically or via chemical synthesis. The nucleotides may be converted to their 5'-O-dimethoxytrityl-3'-(N,N-diisopropyl) phosphoramidite cyanoethyl ester derivatives, and incorporated into synthetic oligonucleotides following the procedures in "Oligonucleotide Synthesis: A Practical Approach", supra. The N-protecting groups are then removed, along with the other oligonucleotide blocking groups, by post-synthesis aminolysis, by procedures generally known in the art.

In a preferred embodiment, the activated nucleotides may be used directly on an automated DNA synthesizer according to the procedures and instructions of the particular synthesizer employed. The oligonucleotides may be prepared on the synthesizer using the standard commercial phosphoramidite or H-phosphonate chemistries.

A moiety containing the leaving group, such as a haloacyl group, or —CO—(CH₂)ₘ—(X)ₙ—N(R₁)—(CH₂)ₚ—L group (even more preferably a CO—(CH₂)₃—C₆H₄—N—[CH₂CH₂Cl]₂) may be added to the aminoalkyl or like tails (—CH₂)_q—Y) following incorporation into oligonucleotides and removal of any blocking groups.

In the situations where the cross linking agent (A-L moiety) is attached to the 3' or 5' terminus of the oligonucleotide, for example by an alkylamine linkage of the formula —$(CH_2)_q$—Y (Y terminating in an amine), the oligonuclotide synthesis may be performed to first yield the oligonucleotide with said aminoalkyl tail, to which then an alkylating moiety, such as the above-noted haloacylgroup or —CO—$(CH_2)_m$—$(X)_n$—$N(R_1)$—$(CH_2)_p$—L is introduced.

An exemplary preferred embodiment of an ODN-MGB conjugate which has a cross-linking agent attached to one of the nucleotide bases is represented by the formula below:

5'-
GGTTATTTTTGAAGATACGAATTTC<u>U</u>CCAGAGACACAGCAGGATTTGTCA—
CDPI₃ where the underlined symbol "U" (the 26th nucleotide unit in the 50 mer) represents a 5-(3-aminopropyl)-2'-deoxyuridine which has a chlorambucil residue attached to the amino group. The symbol "CDPI₃" represents a minor groove binder moiety as described below in connection with Reaction Scheme 1. The 5-(3-aminopropyl)-2'-deoxyuridine component is incorporated into the ODN by using 5'-O-trityl-5-trifluoroacetamidopropyl-2'-deoxyuridine 3'-(N,N-diisopropyl-cyanoethyl-phosphoramidite in accordance with the procedure of Gibson, K. J., & Benkovic, S. J. (1987) Nucleic Acids Res. 15, 6455. The chlorambucil residue and the minor groove binder moiety are introduced into the ODN as described in the experimental section below.

Synthesis of minor groove binder moieties and ODN-MGB conjugates

Presently most preferred embodiments of the minor groove binder moieties of the present invention are "oligopeptides" derived from 1,2-dihydro-3H-pyrrolo [3,2-e] indole-7-carboxylic acid (CDPI) and from 4-amino-<u>N</u>-methylpyrrole-2-carboxylic acid. These are synthetic peptides which have repeating units of the structures shown respectively in Formula 2 and Formula 4 where the degree of polymerization (m) of the peptide is preferably 3 to 5, most preferably 5 for the peptide of Formula 2 and 3 for the peptide of Formula 4. Reaction Scheme 1 discloses a process for preparing a specific tripeptide abbreviated "CDPI₃" which thereafter can be coupled with or without minor modification, to ODNs, to form preferred embodiments of the ODN-MGB conjugates of the present invention.

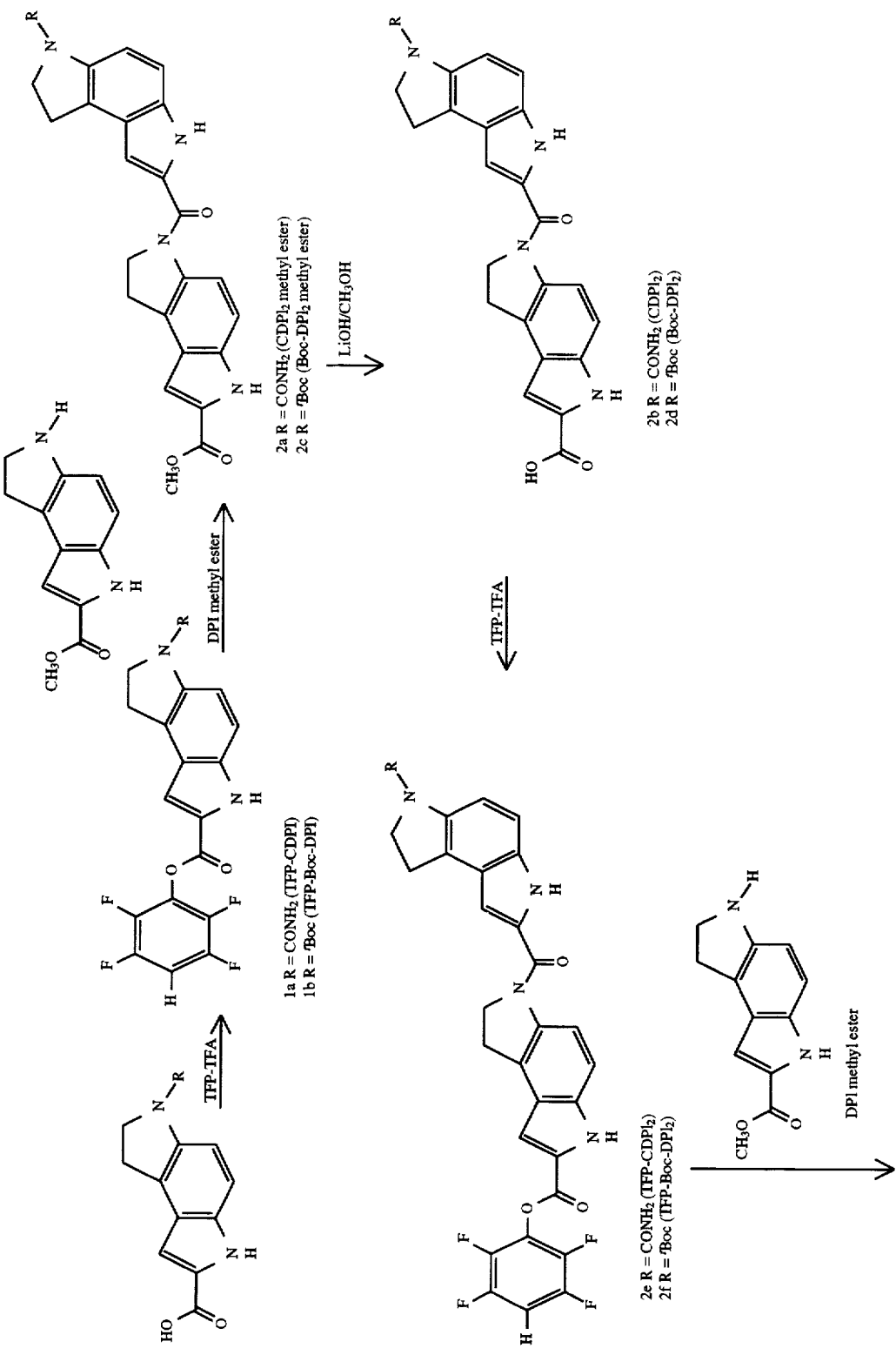

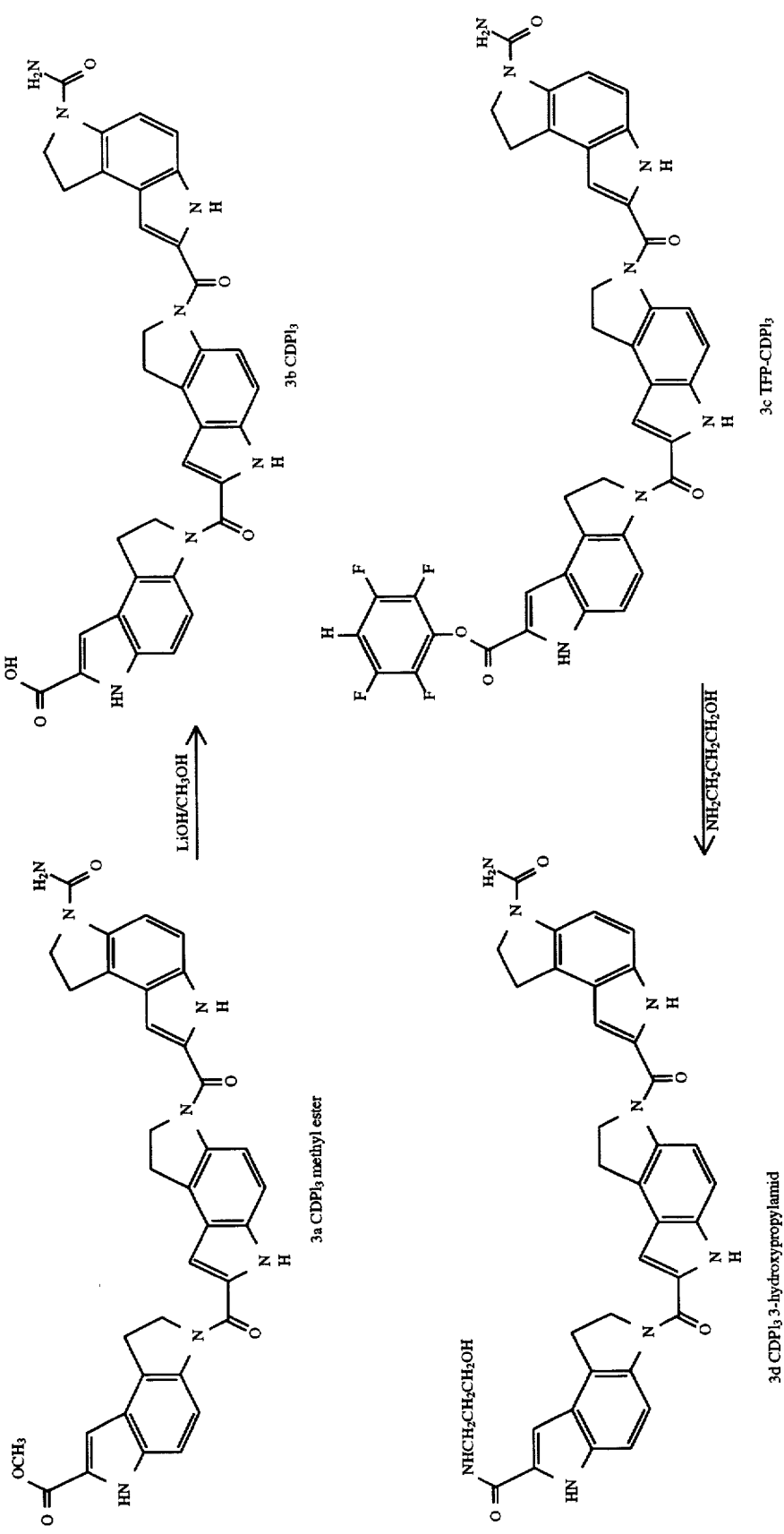

Referring thus to Reaction Scheme 1, the starting material in this synthetic scheme is 3-carbamoyl-1,2-dihydro-3H-pyrrolo|3,2-e|indole-7-carboxylic acid or 3-t-butyloxycarbonyl-1,2-dihydro-3H-pyrrolo|3,2-e|indole-7-carboxylic acid which can be made in accordance with the chemical literature (D. L. Boger, R. S. Coleman, and B. J. Invergo. J. Org. Chem., 1987, Vol.52, 1521–1530). The starting compounds are converted into an active ester by treatment with the tetrafluorophenyl ester of trifluoroacetic acid (TFP-TFA). In compound 1a shown in the scheme the R group is CONH$_2$, in 1b R is t-butyloxycarbonyl ('Boc). The t-butyloxycarbonyl ('Boc) group is a well known protecting group for amino functions which can be removed by acid. The resulting activated esters 1a and 1b are reacted with methyl 1,2-dihydro-3H-pyrroloindole-7-carboxylate (also available in accordance with the chemical literature, see D. L. Boger, R. S. Coleman, and B. J. Invergo. J. Org. Chem., 1987, Vol. 52, 1521–1530) to yield the "dimer" peptide compounds 2a and 2c. The methyl group of the carboxyl function is removed by treatment with base to yield the "dimer" peptides wherein the carboxylic acid group is free. This dimer is activated once more to form an active ester with tetrafluorophenol (2e when R=CONH$_2$, TFP-CDPI$_2$; and 2f when R='Boc, TFP-'Boc-CDPI$_2$). After activation with TFP-TFA the active ester of the dimer can be used for forming the ODN-MGB conjugate as is described below in connection with the corresponding trimer. The activated ester of the dimer peptide can also be reacted with yet another molecule of methyl 1,2-dihydro-3H-pyrroloindole-7-carboxylate to form a "trimer peptide" that has its carboxylic acid function protected as a methyl ester, 3a (methyl 3-carbamoyl-1,2-dihydro-3H-pyrrolo|3,2-e|indole-7-carboxylate trimer). The methyl group is removed by treatment with base and the resulting "trimer peptide" 3b is converted again into an active tetrafluorophenyl ester 3c (2,3,5,6-tetrafluorophenyl 3-carbamoyl-1,2-dihydro-3H-pyrrolo|3,2-e|indole-7-carboxylate trimer, TFP-CDPI$_3$). The active tetrafluorophenyl ester 3c can be used to further lengthen the peptide chain by repeating the steps of reacting with methyl 1,2-dihydro-3H-pyrroloindole-7-carboxylate, saponifying the resulting methyl ester, and if desired, reacting with TFP-TFA again to make the active tetrafluorophenyl ester of the peptide incorporating 4 CDPI moeieties. As it will be readily understood, these steps can be repeated further until the desired number of CDPI moieties are included in the peptide. In the herein described preferred embodiments the active tetrafluorophenyl ester of the tripeptide 3c (TFP-CDPI$_3$) is utilized for coupling to an ODN to make an ODN-MGB, or for synthesizing an ODN-MGB on a suitable modified controlled pore glass (CPG) solid support as is described below in connection with Reaction Schemes 4 and 5. Reaction Scheme 1 indicates as its last step the preparation of a hydroxylpropylamide derivative from the the active tetrafluorophenyl ester of the tripeptide 3c (TFP-CDPI$_3$). The hydroxylpropylamide derivative of the tripeptide 3d (3-carbamoyl-1,2-dihydro-3H-pyrrolo[3,2-e|indole-7-carbox]-1-amido-3-propanol trimer, CDPI$_3$-3-hydroxylpropylamide) can be used for coupling with an ODN to obtain an ODN-MGB in accordance with the present invention. The tripeptide 3d however, was also used as a "free standing" minor groove binder molecule as a control in certain binding studies which are described below.

Reaction Scheme 2

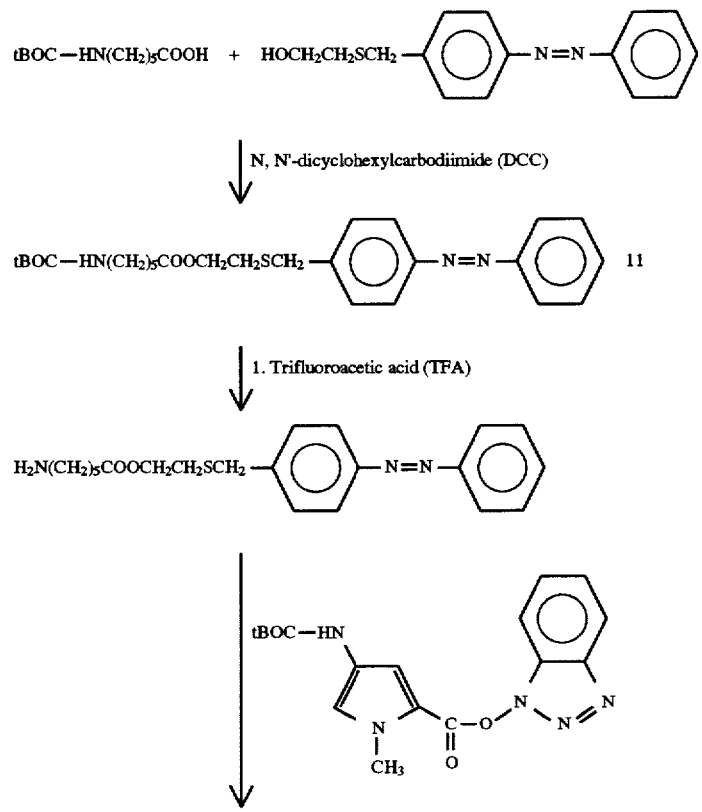

-continued
Reaction Scheme 2

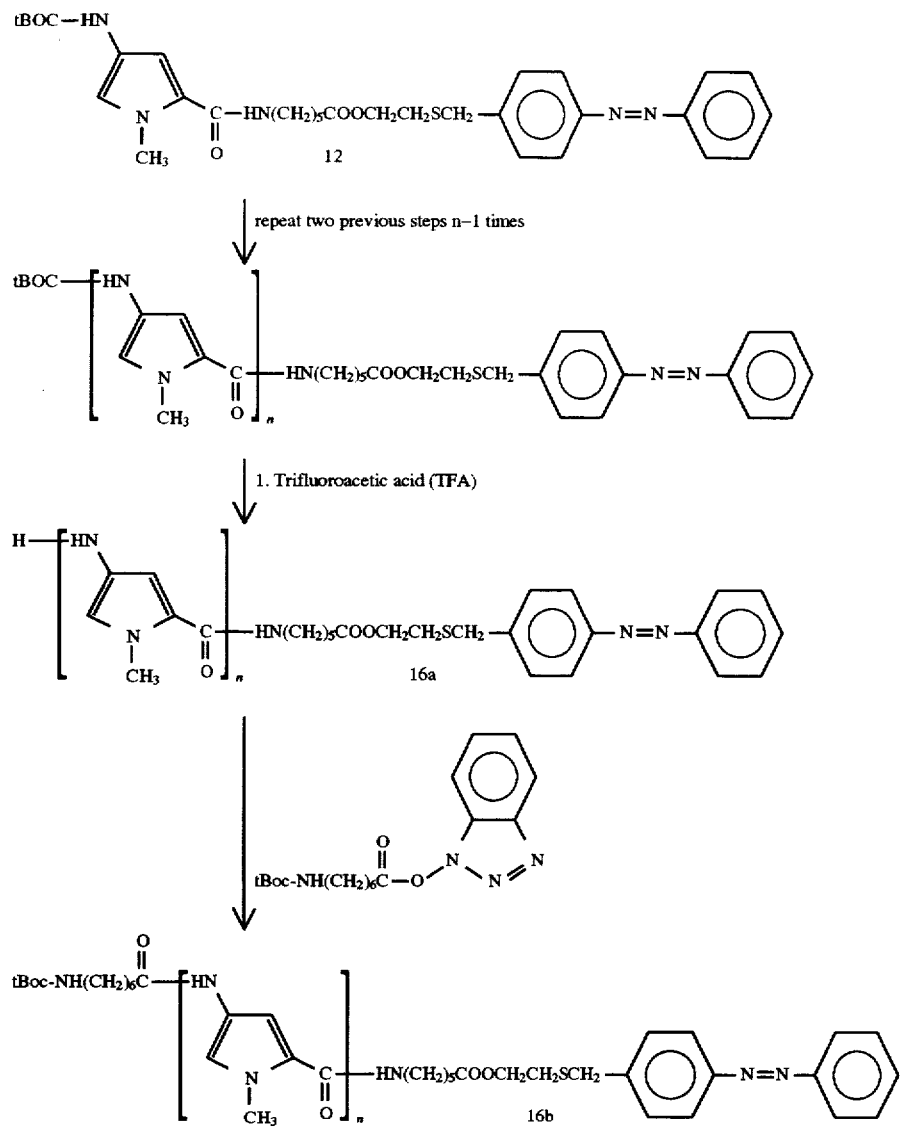

Referring now to Reaction Scheme 2 the synthesis of another preferred embodiment of the minor groove binder peptides is disclosed, where the "monomer" is the residue of 4-amino-N-methylpyrrol-2-carboxylic acid, and which embodiment also bears a reporter group/containing a diazobenzene moiety. Thus, in accordance with this scheme 6-[(tert-butyloxy) carboxamido]hexanoic acid is condensed in the presence of N,N-dicyclohexylcarbodiimide with 2-[4-(phenylazo)-benzylthio]ethanol to form (2-[4-(phenylazo)benzylthio]ethyl 5-[(tert-butyloxy) carboxamido]pentylcarboxylate, 11). The 'Boc protecting group is removed from compound 11 by treatment with trifluoroacetic acid (TFA) and the resulting compound having a free amino function is reacted with an activated ester of 'Boc protected 4-amino-N-methylpyrrol- 2-carboxylic acid. The latter activated ester compound (1,2,3-benzotriazol-1-yl 1-methyl-4-(tert-butyloxy)carboxamido-pyrrole-2-carboxylate) is made from 1-methyl-4-[tert-butyloxy)carboxamido]pyrrole-2-carboxylic acid which is available pursuant to the literature procedure of L. Grehn, V. Ragnarsson, *J. Org. Chem.*, 1981, 46, 3492–3497. The resulting 2-[4-(phenylazo)benzylthio]ethyl 5-[1-methyl-4-(tert-butyloxy)carboxamido]pyrrole-2-carboxamido]pentylcarboxylate, 12) has one unit of the monomer "2-amino-N-methylpyrrol carboxylic acid" residue attached to the reporter group that carries the diazobenzene moiety. After removal of the 'Boc protecting group with trifluoroacetic acid and coupling with one or more molecules of 1,2,3-benzotriazol-1-yl 1-methyl-4-(tert-butyloxy)carboxamido-pyrrole-2-carboxylate can be accomplished, until a peptide containing the desired number of monomer residues is obtained. Such a compound having n number of monomers and a free amino group is indicated in Reaction Scheme 2 as 16a. Compound 16a can be reacted with an activated ester (such as a 1,2,3-benzotriazol-1-yl activated ester) of 'Boc protected 6-aminohexanoic acid to provide the oligopeptide shown as compound 16b in Reaction Scheme 2. The 'Boc protecting group can be removed from the latter compound under acidic conditions, and the resulting derivative having a free amino function can be attached by conventional synthetic methods to either the 3'-phosphate or 5'-phosphate end of an ODN. Alternatively, the derivative having a free amino function can also be attached to the 3' or 5'-OH end of an oligonucleotide using a variety of bifunctional linking groups, as discussed above.

5'-amino tailed ODN. The example shown in the scheme is that of the TFP ester of the tripeptide derived from

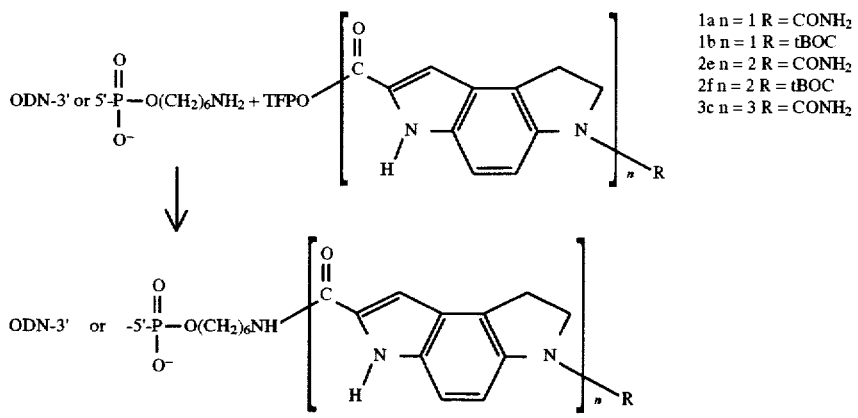

1a n = 1 R = CONH₂
1b n = 1 R = tBOC
2e n = 2 R = CONH₂
2f n = 2 R = tBOC
3c n = 3 R = CONH₂

Reaction Scheme 3

Referring now to Reaction Scheme 3 a general method for coupling a 3'-amino tailed or 5'-amino-tailed ODN with the tetrafluorophenyl (TFP) ester activated exemplary minor groove binding oligopeptides is illustrated. Although the scheme shows the use of the TFP activated exemplary minor groove binding compounds obtained in accordance with Reaction Scheme 1, it should be kept in mind that this general method is suitable for the coupling of other TFP activated minor groove binding compounds with ODNs, as well. The reference numeral 1a through 3c in Reaction Scheme 3 refer to the exemplary compounds obtained in accordance with Reaction Scheme 1.

The 3'- or 5'-amino tailed ODNs can be synthesized by conventional methods; for example an aminohexyl residue can be attached to either end of the ODN by using commercially available N-monomethoxytritylaminohexyl phosphoramidite. Alternatively, the amino tailed ODNs can be synthesized in accordance with the methods described in application Ser. No. 08/090,408 filed on Jul. 12, 1993 which has been allowed and the issue fee was paid. The specification of application Ser. No. 08/090,408 is expressly incorporated herein by reference. In accordance with the present scheme the amino tailed ODN is converted into a cetyltrimethylammonium salt to render it soluble in organic solvents, and the tetrafluorophenyl ester activated minor groove binder molecule is condensed therewith, preferably in DMSO as a solvent.

CPG bearing 5'-amino tailed ODN

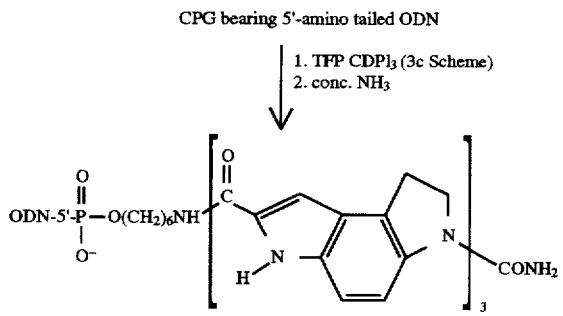

Reaction Scheme 4

Reaction Scheme 4 discloses another method of coupling an active ester of a minor groove binder molecule to a 5'-amino tailed ODN. The example shown in the scheme is that of the TFP ester of the tripeptide derived from 3-carbomoyl-1,2-dihydro-3H-pyrrolo[3,2-e]indole-7-carboxylic acid residues (TFP-CDPI₃) but it should be understood that the generic principles disclosed in connection with this reaction scheme can be used with other minor groove binder molecules as well. In this method, the ODN is still attached to a CPG support, and has a free amino group on its "amino tail". This can be obtained by using N-monomethoxytritylaminohexyl phosphoramidite mentioned above. The monomethoxytrityl group is removed after the coupling of the phosphoramidite to give the desired CPG-bearing-"amino-tailed ODN". Alternatively, such a CPG- can be obtained in accordance with the disclosure of the above-cited application Ser. No. 08/090,408, and references cited therein. By way of summary, the ODN is synthesized stepwise attached to the CPG, and having a tail having an amino group protected with a 9-fluorenylmethoxycarbonyl (Fmoc) group. After the desired sequence of nucleotides has been built up, the Fmoc group is removed from the amino group while the ODN is still attached to the CPG support. In accordance with Reaction Scheme 4 of the present invention this "CPG-bearing-amino-tailed-ODN" having the free amino group is condensed with the active ester (TFP-CDPI₃, 3c) or with a like activated form of a minor groove binder. The ODB-MGB conjugate is thereafter removed from the CPG support by conventional methods, most frequently by treatment with ammonia.

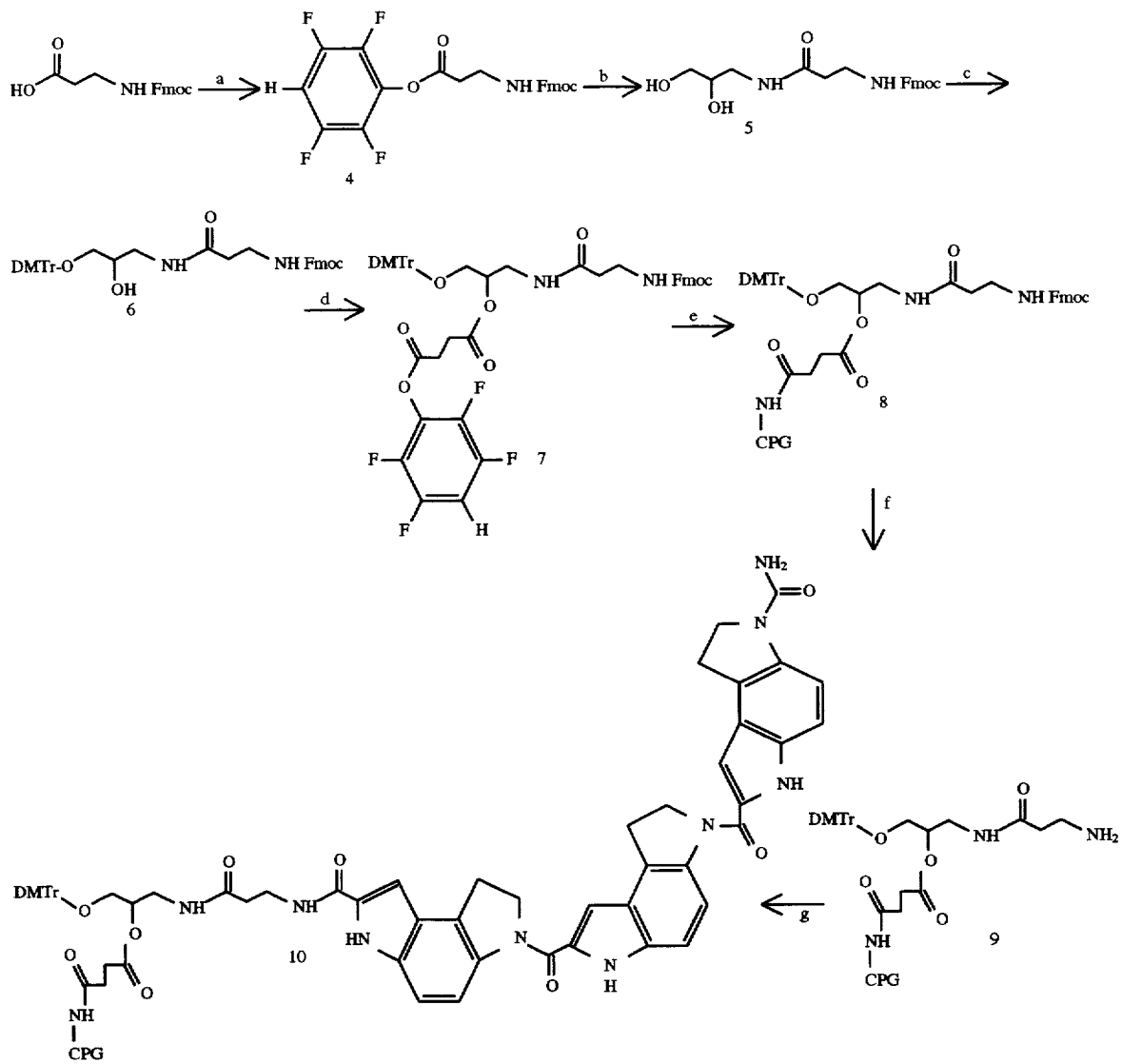

*Reagents: (a) TFP-TFA, Et₃N, CH₂Cl₂; (b) 3-amino-1,2-propanediol, CH₂Cl₂;
(c) DMTrCl, pyridine; (d) succinic anhydride, N-methylamidazole, CH₂Cl₂, TFP-TFA
(e) Alkyl amine CPG, pyridine; (f) piperadine, DMF; (g) TFP-CDPI₃ (3c Scheme 1), DMF.

Reaction Scheme 5 discloses another preferred method for preparing the ODN-MGBs of the present invention. More particularly, Reaction Scheme 5 discloses the preferred synthetic process for preparing ODN-MGBs by first attaching a linking molecule to a CPG support, thereafter attaching an activated form of minor groove binder to the linking molecule, and thereafter building the ODN of desired sequence step-by-step in an automatic ODN synthesizer using the just described modified CPG support. The ODN-MGB conjugate is removed from the CPG support only after the ODN moiety of desired sequence has been completed. The linking molecule in this case is a trifunctional molecule, with each function having different reactivity, which permit attachment to the CPG, reaction with the activated form of minor groove binder moiety and the building of the ODN portion, each using a different functionality of the linking molecule. A more general and detailed description of this synthetic method and of the trifunctional linking molecules which can be utilized in the method, but without any reference to minor groove binders, can be found in application Ser. No. 08/090,408. Reaction Scheme 5 illustrates this synthetic process with the example of β-alanilyl-3-amino-1,2-propanediol as the trifunctional linking molecule, and TFP-CDPI₃ (compound 3c) as the activated form of the minor groove binder.

Thus in accordance with Reaction Scheme 5, Fmoc protected β-alanine is reacted with tetrafluorophenyl trifluoroacetate (TFP-TFA) to provide 2,3,5,6-tetrafluorophenyl 3-[N-(9-fluorenylmethoxycarbonyl)] aminopropionate (4). The active ester 4 is reacted with 3-amino-1,2-propanediol to provide 1-[3-[N-(9-fluorenylmethoxycarbonyl)amino]-1-oxopropyl]amino-(R,S)-2,3-propanediol (5). The primary hydroxyl group of 5 is thereafter protected with a dimethoxytrityl group to give 1-[3-[N-(9-fluorenylmethoxycarbonyl)-amino]-1-oxopropyl]amino-(R,S)-2-[[bis(methoxyphenyl)phenylmethoxy]metyl]-2-ethanol (6). The secondary hydroxyl group of compound 6 is reacted with succinic anhydride and the carboxylic group in the resulting compound is thereafter converted into an active ester, 2,3,5,6-tetrafluorophenyl 1-|3-|N-(9-fluorenylmethoxycarbonyl)amino|-1-oxopropyl|amino-(R,S)-2-||bis(methoxyphenyl)phenylmethoxy|metyl|-2-ethyl butanedioate (7). Compound 7 is then attached to a long chain aminoalkyl controlled pore glass support (LCAA-CPG, or alkylamine CPG) which is commercially available and is described in the above-cited application Ser. No. 08/090,408. The resulting "modified CPG" is shown in Reaction Scheme 5 as Compound 8. The Fmoc protecting group is removed from 8 by treatment with mild base (piperidine in dimethylformamide) to yield the "modified CPG" 9 that has a free primary amine function as part of the linking molecule. In the next step the activated minor groove binder molecule, in this instance TFP-CDPI$_3$ (compound 3c) is reacted with the primary amine function of 9, to yield the modified CPG 10 that includes the minor groove binder moiety and still has the primary hydroxyl group of the linking group protected with a dimethoxytrityl group. Although this is not shown in Reaction Scheme 5, in the subsequent steps the dimethoxytrityl group is removed and the ODN synthesis is performed in an automatic synthesizer, by steps which are now considered conventional in the art. When the synthesis is complete the ODN-MGB conjugate is removed from the CPG support by treatment with ammonia. The latter step cleaves the bond attaching the secondary hydroxyl group of the 3-amino-1,2-propanediol moiety to the CPG support.

Biological Testing and Discussion

The ODN-MGB conjugates bind to single stranded DNA. They also bind to double stranded DNA in the presence of a recombinase enzyme, and in some cases to single stranded RNA and DNA and RNA hybrids as well. The binding however occurs only if the ODN moiety is complementary, or substantially complementary in the Watson-Crick sense, to a target sequence in the target DNA or RNA. When this condition is met, the binding of the ODN-MGB to the target sequence is significantly stronger than binding of the same ODN would be without the minor groove binder. The foregoing is demonstrated by the tests described below, and provides utility for the ODN-MGB conjugates of the present invention as analytical and diagnostic hybridization probes for target DNA or RNA sequences, and in therapeutic antisense and anti-gene applications.

TABLE 1

$T_m$'s data of the (dAp)$_8$ + (dTp)$_8$ duplex carrying intercalators or oligo-(1-methyl-2-carboxy-4amino)pyrrole residues attached to 3'-end of the ODN.[a]

| COMPLEX | | $T_m$ | $\Delta T_m$[b] |
|---|---|---|---|
| (dAp)$_8$ + (dTp)$_8$ | | 21.1 | — |
| (dAp)$_8$ + (dTp)$_8$ + Distamycin A[c] | | 47.1 | 26.0 |
| (dAp)$_8$ + (dTp)$_8$-X$_m$ | m = 2 | 39.4 | 18.3 |
| | m = 3 | 51.7 | 30.6 |
| | m = 4 | 60.2 | 39.1 |
| | m = 5 | 65.4 | 44.3 |
| (dTp)$_8$ + (dAp)$_8$-X$_m$ | m = 2 | 29.1 | 8.0 |
| | m = 3 | 39.0 | 17.9 |
| | m = 4 | 42.7 | 21.6 |
| | m = 5 | 52.6 | 31.5 |
| (dAp)$_8$-Y + (dTp)$_8$ | | 30.5 | 9.4 |
| (dAp)$_8$-Y + (dTp)$_8$-Y[d] | | 42.9 | 21.8 |

[a]Reported parameters are averages of at least three experiments. Optical melts were conducted in 0.2 M NaCl, 0.1 mM EDTA, 0.01 M (±0.1° C.) Na$_2$HPO$_4$, pH 7.0 with [(dTp)$_8$–(dAp)$_8$] = 2.5 · 10$^{-5}$ M.
[b]The difference in $T_m$ between modified and unmodified duplexes.
[c]Concentration of distamycin A was 2.5 · 10$^{-5}$ M.
[d]Ethidium bromide (EtBr) was conjugated by its 8-NH$_2$-position to the 3'-terminal phosphate of the ODNs through a β-alanine linker by the method in ref 12.

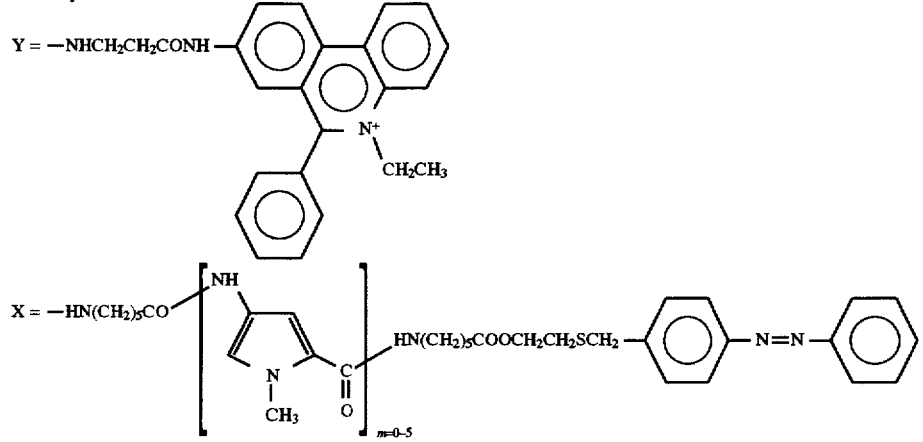

Table 1 illustrates the melting temperature of several complexes formed of complementary oligonucleotides which have the minor groove binder moiety derived from 4-amino-N-methylpyrrol-2-carboxylic acid residues. The minor groove binder moiety is specifically shown as the radical X by the formula below Table 1. It is noted that the radical X also includes a linking moiety which is derived from 6-aminohexanoic acid. The oligonucleotides utilized here are 8-mers of 2'-deoxyadenylic acid, and 8-mers of thymidylic acid. The minor groove binder X is attached to the ODNs at the 3'-phosphate end, the 5'-end of these ODNs have no phosphate. In this regard it is noted that the ODNs are abbreviated in these and the other tables in the manner customary in the art. The group Y symbolizes an ethidium bromide moiety attached to the 3' phosphate end through a "β-alanine" linking moiety. The Y group represents an intercalating group and acts as a control for comparison with the minor groove binding groups. The symbol m represents the number of 4-amino-N-methyl-pyrrol-2-carboxylic acid residues present in each ODN-MGB of the table.

As is known in the art, the melting temperature ($T_m$) of an oligonucleotide or polynucleotide duplex is defined as that temperature at which 50% of the respective oligonucleotide or polynucleotide is dissociated from its duplex, Watson Crick hydrogen bonded form. A higher melting temperature ($T_m$) means a more stable duplex. As is known further, the melting temperature of an oligonucleotide or polynucleotide is dependent on the concentration of the nucleotide in the solution in which the melting temperature is measured, with higher concentrations resulting in higher measured melting temperatures. The melting temperatures indicated in these tables were measured under conditions indicated in the table and in the experimental section. $\Delta T_m$ represents the change in melting temperature of the modified duplex relative to the melting temperature of the $(dAp)_8 \cdot (dTp)_8$ complex which has no minor groove binder moiety.

As it can be seen from Table 1, the covalently bound minor groove binder moiety significantly increases the stability (melting temperature Tm) of the complex, whether the group X (minor groove binder moiety) is attached to the $(dTp)_8$ or to the $(dAp)_8$ oligonucleotide. In this instance the greatest degree of stabilization (highest melting temperature) is achieved when the minor groove binder moiety is a 5-mer oligopeptide. In the comparative experiment when the intercalating group Y is attached to the $(dAp)_8$ oligomer, a comparatively much smaller degree of stabilization is attained. Even attaching the intercalating Y group to each of the two strands of oligomers in this experiment, raised the melting temperature less than the minor groove binder moiety having five 4-amino-N-methylpyrrol-2-carboxylic acid residues.

TABLE 2

$T_m$'s data of the duplexes formed by hexadeca-, octathymidylate and their oligo-(1-methyl-2-carboxy-4amino)pyrrole derivatives with polydeoxyriboadenylic acid in 0.2 M NaCl, 0.01 M $Na_2HPO_4$, 0.1 mM EDTA (pH 7.0). X is same as Table 1.

| Oligo Derivative | | $T_m$ °C. | $\Delta T_m$ °C. |
|---|---|---|---|
| $(dTp)_{16}$ | | 48.5 | — |
| $(dTp)_{16}$-$NH(CH_2)_6COOH$ | | 49 | 0.5 |
| $(dTp)_{16}$-X | m = 1 | 49.3 | 0.8 |
| | m = 2 | 55.6 | 7.1 |
| | m = 3 | 61 | 12.5 |
| | m = 4 | 66 | 17.5 |
| | m = 5 | 68 | 19.5 |
| $(dTp)_8$ | | 28 | — |
| $(dTp)_8$-X | m = 1 | 28 | 0 |
| | m = 2 | 40 | 12 |
| | m = 3 | 52 | 24 |
| | m = 4 | 60 | 32 |
| | m = 5 | 66 | 38 |

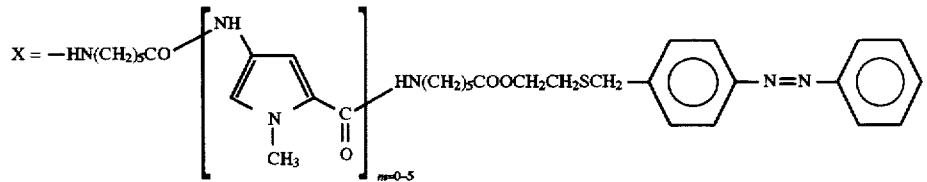

Table 2 discloses information in a manner similar to Table 1. In the tests reported in this table 16-mer ODNs of thymidylic acid having the minor groove binder moiety represented by X (X is the same as in Table 1) were complexed with polydeoxyriboadenylic acid. As a comparative control a 16 mer ODN of thymidylic acid $(dTp)_{16}$ connected at its 3'-phosphate end to 6-aminohexanoic acid was also tested. Additionally an 8-mer of thymidylic acid $(dTp)_8$ and its conjugates with the minor groove binders of varying peptide length were also tested. In these tests too, the minor groove binder attached to the ODN causes significant stabilization of the complex between the ODN-MGB and the complementary DNA strand. Greatest stabilization occurs when the number of 4-amino-N-methylpyrrol-2-carboxylic acid residues in the minor groove binder moiety is five. In contrast, the aminohexanoic acid tail on the 16-mer ODN results in virtually no stabilization of the complex.

TABLE 3

Melting temperatures (°C.) of duplexes formed by poly(dA) and poly(rA) with $(Tp)_8$ strands terminally linked to $CDPI_{1-3}$ and $BocDPI_{1-2}$ ligands.[a]

| Octathymidylate | poly(dA) | | poly(rA) | |
|---|---|---|---|---|
| derivative | $T_m$ | $\Delta T_m$ | $T_m$ | $\Delta T_m$ |
| $(dTp)_7dTp$-L1 | 25 | — | 13 | — |
| $(dTp)_7dTp$-L1-X m = 1 | 34 | 9 | 18 | 5 |
| $(dTp)_7dTp$-L1-X m = 2 | 50 | 25 | —[b] | — |
| $(dTp)_7dTp$-L1-X m = 3 | 68(65) | 43(40) | 32(31) | 19(18) |
| $(dTp)_7dTp$-L1-Y m = 1 | 26 | 1 | 12 | -1 |
| $(dTp)_7dTp$-L1-Y m = 2 | 43 | 18 | 17 | 4 |

TABLE 3-continued

Melting temperatures (°C.) of duplexes formed by poly(dA) and poly(rA) with (Tp)$_8$ strands terminally linked to CDPI$_{1-3}$ and BocDPI$_{1-2}$ ligands.[a]

| Octathymidylate | poly(dA) | | poly(rA) | |
|---|---|---|---|---|
| derivative | $T_m$ | $\Delta T_m$ | $T_m$ | $\Delta T_m$ |
| L1-pdT(pdT)$_7$ | 24 | — | 12 | — |
| X-L1-pdT(pdT)$_7$ m = 1 | 31 | 7 | 14 | 2 |
| X-L1-pdT(pdT)$_7$ m = 2 | 49 | 25 | —[b] | — |
| X-L1-pdT(pdT)$_7$ m = 3 | 68 | 44 | 35 | 23 |
| Y-L1-pdT(pdT)$_7$ m = 1 | 23 | −1 | 9 | −3 |
| Y-L1-pdT(pdT)$_7$ m = 2 | 41 | 17 | 19 | 7 |

[a]The data in brackets were obtained for the derivative with linker L2.
[b]No melting transition was observed.

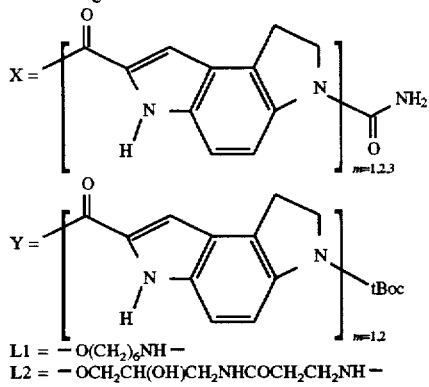

L1 = —O(CH$_2$)$_6$NH—
L2 = —OCH$_2$CH(OH)CH$_2$NHCOCH$_2$CH$_2$NH—

Table 3 discloses melting temperature ($T_m$) and change in melting temperature ($\Delta T_m$) data in tests where the oligonucleotide is an 8-mer of thymidylic acid having a minor groove binder moiety attached to it either at the 5'-phosphate or 3'-phosphate end, as indicated in the table. The minor groove binder moieties represented here by X and Y are "oligopeptides" based on the residue of 1,2-dihydro-3H-pyrrolo[3,2-e]indole-7-carboxylic acid (CDPI or BocDPI) and their structures are shown in the table. These minor groove binding oligopeptides are attached to the ODN through a linking moiety "L1 or L2" the structures of which are also shown below the table. The ODN-MGB conjugates were incubated with a complementary ribo- or deoxyribo homopolymer. Thus for ODN-MGB conjugates comprising ODNs of thymidylic acid, poly A or poly-dA was used. The change in melting temperature ($\Delta T_m$) is indicated relative to the complex with the ODN which bears the corresponding linking group L1 or L2 in the corresponding end of the ODN, but bears no minor groove binding moiety. As it can be seen from Table 3, these ODN-MGB complexes again exhibit significant stabilization of the complex with the complementary deoxyribo homopolymer, with the greatest stabilization occurring in these tests when the minor groove binding moiety has 3 CDPI units. Surprisingly, stabilization of the complex occurs even when the ODN-MGB is incubated with a complementary ribohomopolymer. This is surprising because it had been generally observed in the prior art that free standing minor groove binding molecules do not bind to DNA-RNA hybrids.

TABLE 4

$T_m$'s data (°C.) of heterogeneous duplexes phosphodiester and phosphorothioate backbones and oligo(pyrroloindole carboxamide) peptide residues attached to the different positions[a].

| | | Derivative of CpApTpCpCpGpCpT | | | Derivative of ApGpCpGpGpApTpG | | | |
|---|---|---|---|---|---|---|---|---|
| | Type of | | | | DNA | | | |
| | terminal | | | | | 3'-L2-X & | 2'-DNA PS[c] | |
| Type of Backbone | modification | 3'-L1- | 3'-L2-X | 5'-X-L1- | 5'-X-L1- | none[b] | 5'-X-L1- | 3'-L2-X |
| DNA | 3'-L1- | 41 | 52 | 45 | 50 | 33 | 27 | 40 |
| | 3'-L2-X | 57 | 81 | 78 | 77 | 50 | 73 | 77 |
| | 5'-X-L1- | 58 | 79 | 76 | 76 | 49 | 70 | 75 |
| | 3'-L2-X 5'-X-L1- | 60 | 72 | — | 65 | — | — | — |
| 2'-DNA PS[c] | none[b] | 32 | 43 | 32 | — | 24 | 16 | 28 |
| | 5'-X-L1 | 38 | 69 | 67 | — | 28 | 62 | 63 |
| | 3'-L2-X | 45 | 74 | 71 | — | 36 | 64 | 69 |

[a]Concentration of ODNs in the melting mixtures was 2 × 10$^{-6}$ M in 140 mM KCl, 10 mM MgCl$_2$, 20 mM HEPES-HCl (pH 7.2).
[b]The ODN has free 3'- and 5'-OH groups.
[c]PS is phosphorothioate linkage

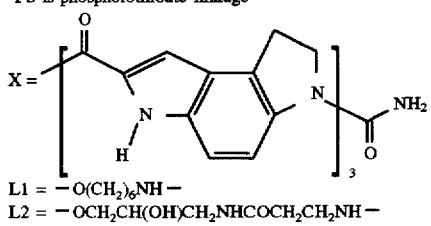

L1 = —O(CH$_2$)$_6$NH—
L2 = —OCH$_2$CH(OH)CH$_2$NHCOCH$_2$CH$_2$NH—

Table 4 discloses results of a study of duplex formation between derivatives of two complementary octamers: CpApTpCpCpGpCpT and ApGpCpGpGpApTpG. Each octamer was modified, as shown in the table, so that hybridization of the corresponding oligodeoxyribonucleotides and of oligodeoxyribonucleotides having a phosphorothioate backbone were examined. The ODN also had the tripeptide based on the residues of 1,2-dihydro-3H-pyrrolo[3,2-e] indole-7-carboxylic acid (CDPI) (minor groove binder moiety X) attached either to the 3' or to the 5' end (as indicated) through a linking group of the structure L1 or L2. (X, L1 and L2 are the same as in Table 3.) As controls, the melting temperature of duplexes was also determined for duplexes where the ODNs bore only the linking groups. As it can be seen in the table, the duplexes are significantly stabilized by the presence of a minor groove binder moiety, and greater stabilization occurs when each strand of the duplex has a covalently bound minor groove binder.

TABLE 5

$T_m$'s data (°C.) of heterogeneous duplexes carrying 3'-oligo(pyrroloindole carboxamide) peptide residues.

| Complementary ODNs | | d(AGCGGATG)p | | d(AICIIATT)p | |
|---|---|---|---|---|---|
| | | 3'-L1- | 3'-L2-X | 3'-L1- | 3'-L1-X |
| d(CATCCGCT)p | 3'-L1- | 41 | 52 | 11 | — |
| | 3'-L2-X | 57 | 81 | 48 | 67 |
| d(CATCCICT)p | 3'-L1- | 31 | 48 | -0 | 41 |
| | 3'-L1-X | 54 | 79 | 48 | 63 |

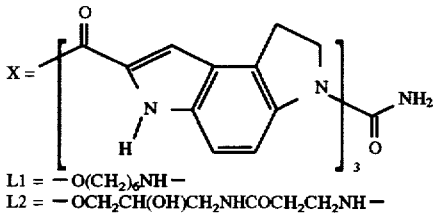

L1 = —O(CH₂)₆NH—
L2 = —OCH₂CH(OH)CH₂NHCOCH₂CH₂NH—

Table 5 discloses melting temperature data obtained when complementary or "quasi complementary" ODN-MGB were incubated and examined for duplex formation. The minor groove binding moiety X and the linking groups L1 and L2 are shown in the table and are the same as in Tables 3 and 4. As anticipated, when guanine is replaced inosine (I) in the strands the binding of the duplexes is very weak ($T_m$ is approximately 0° C.) if there is no minor groove binding moiety present. However, when guanine is replaced by inosine in the oligonucleotides the presence of one covalently appended minor groove binder X stabilized the hybrid by almost 50° C. and the presence of two such minor groove binders in antiparallel orientation provided 63° C. of stabilization. When the same strands contained guanine, one minor groove binder increased the $T_m$ by 15° C. while two increased it by nearly 45° C. To the knowledge of the present inventors a $T_m$ of 81° C. for an 8 mer is unprecedented in the prior art.

Primer Extension Experiment

That sequence specificity in the Watson-Crick sense of the ODN portion of the ODN-MGB conjugate is required for complexing the ODN-MGB conjugate to a target sequence was demonstrated by a primer extension experiment. In this experiment, primer extension occurs with the enzyme T7 DNA polymerase that works from the 5' end of a template strand. A 16-mer ODN-MGB which was complementary in the Watson Crick sense to a target sequence on the template strand was incubated with a long single stranded DNA template and the T7 DNA polymerase enzyme. Blockage of the primer extension was noted at the site of binding with the ODN-MGB when the minor groove binding moiety was on the 5' end of the 16-mer ODN. The minor groove binder was the pyrroloindole tripeptide shown in this application in Table 5. When there was a single mismatch in the sequence specificity of the 16-mer to the target, primer extension was not blocked. Primer extension was also not blocked when the minor groove binder moiety was attached to the 3' end of the 16-mer. Primer extension was also not blocked when the sequence specific 16-mer and the free minor groove binder molecule (Compound 3d, not covalently attached to the ODN) was incubated with the template and the enzyme. These experiments show that sequence specificity of the ODN-MGB is important for complex formation, and that the minor groove binding moiety does not simply act as an "anchor" to non-specifically bind the appended ODN to another strand. The ability of ODN-MGB conjugates to inhibit primer extension indicates that these conjugates can be used diagnostically as polymerase chain reaction (PCR) clamping agents. (see Nucleic Acid Research (1993) 21:5332–5336).

Slot-blot hybridization assay

The ODN-MGB conjugates of the present invention are useful as hybridization probes. This is demonstrated by the description of the following experiment utilizing a $^{32}$P-labeled ODN-MGB conjugate as a diagnostic probe. When compared to the same ODN without a covalently linked minor groove binder (MGB) moiety, the conjugate hybridizes to its complement with greater strength, efficiency and specificity. The slot-blot hybridization assay is a widely used DNA probe diagnostic assay, and the attributes of these MGB-ODN conjugates improve the performance of the assay.

Specifically, in the herein described experiment a standard protocol was followed, as described in Protocols for Nucleic Acid Blotting and Hybridization, 1988, Amersham, United Kingdom. Labelled test ODN which hybridized to the immobilized plasmid was quantitated as counts per minute (cpm), and plotted vs temperature of hybridization. Four 16-mer probes complementary to M13mp19 DNA (a phage DNA) were evaluated. Two of these probes were totally complementary to a site in the phage DNA; one of these contained a 3'-conjugated CDPI₃ moiety while the other was unmodified. The second pair of probes were targeted to the same site in M13mp19 DNA but each contained a single mismatch (underlined in drawing FIG. 1). Here again, one ODN was 3'-conjugated to CDPI₃ while the other was unmodified.

The results of the slot hybridization study are shown in FIG. 1. Compared to an unmodified but otherwise identical 16-mer, the CDPI₃-containing probe formed a hybrid with a melting temperature) ($T_m$) of 50° C. versus only 33° C. This higher melting temperature more than doubled the yield of perfectly matched hybrids. When a mismatch was introduced into either probe, stability of the respective hybrids dropped. The CDPI₃-modified probes exhibited good sequence discrimination between 37°–50° C. Furthermore, under the hybridization conditions used here there was no evidence for binding of the CDPI₃ moiety to preexisting double-stranded regions in the M13mp19 DNA target, indicating that totally non-specific binding of these conjugates is not present.

Sequence-specific alkylation of a gene in cultured human cells

The ODN-MGB conjugates of the present invention which also bear a covalently attached alkylating agent can be used as "anti-gene" agents, that is is for the surpression of the expression of undesired (disease causing) genes, provided the ODN-MGB conjugate is complementary to a target sequence in the target gene. In such a case the MGB moiety improves the binding to the double stranded gene (in the presence of a recombinase enzyme) and the alkylating moiety results in permanent covalent binding of the ODN-MGB conjugate to the target sequence.

As a demonstrative experiment the above described 50-mer ODN which was 3' end-modified with a CDPI$_3$ group and internally modified with a nitrogen mustard group (chlorambucil) sequence-specifically crosslinked to the expected site in a targeted gene (HLA DQβ1 0302 allele) present in living human BSM cells (a human B-lymphocyte cell line). The ODN-MGB conjugate was added to a suspension of BSM cells at 1–50 μM final concentration. After 3.5 hr the genomic DNA was extracted and treated with hot pyrrolidine to convert any alkylation events into nicks. Next the targeted region of the 0302 allele was amplified by LM-PCR (ligation mediated-polymerase chain reaction), a technique which can be used to detect cleavage events at single-base resolution. Analysis of the products on a sequencing gel showed that the modified ODN had bound to and alkylated the targeted site. A similar ODN lacking the CDPI$_3$ group was considerably less effective in efficiency of alkylation of the target.

It is probable that in the experiment above the recognition and binding of the ODN-MGB conjugate to homologous double-stranded DNA took place with the assistance of nuclear recombinases. In like experiments and applications endogenous recombinase enzymes can catalyze the sequence specific targeting of double-stranded genomic DNA by ODN-CDPI$_3$ conjugates in other living cells. When these ODNs have an appended crosslinking agent, they can alkylate the targeted DNA. By stabilizing the D-loop formed in the presence of recombinase, the CDPI$_3$ promotes the crosslinkage reaction. The crosslinkage event is a powerful inhibitor of expression of the targeted gene. Thus crosslinking ODN-CDPI$^3$ conjugates can be used as antigene agents.

SPECIFIC EMBODIMENTS, EXPERIMENTAL SECTION

General Experimental

All air and water sensitive reactions were carried out under a slight positive pressure of argon. Anhydrous solvents were obtained from Aldrich (Milwaukee, Wis.). Flash chromatography was performed on 230–400 mesh silica gel. Melting points were determined on a Mel-Temp melting point apparatus in open cappilary and are uncorrected. Elemental analysis was performed by Quantitative Technologies Inc. (Boundbrook, N.J.). UV-visible absorption spectra were recorded in the 200–400-nm range on a UV-2100 (Shimadzu) or a Lambda 2 (Perkin Elmer) spectrophotometers. $^1$H NMR spectra were run at 20° C. on a Bruker WP-200 or on a Varian XL-200 spectrophotometer; chemical shifts are reported in ppm downfield from Me$_4$Si.

2,3,5,6-Tetrafluorophenyl 3-carbamoyl-1,2-dihydro-3H-Pyrrolo[3,2-e]indole-7-carboxylate (1a)

2,3,5,6-Tetrafluorophenyl trifluoroacetate (2.6 g, 10 mmol, H. B. Gamper, M. W. Reed, T. Cox, J. S. Virosco, A. D. Adams, A. A. Gall, J. K. Scholler and R. B. Meyer, Jr. *Nucleic Acids Res.*, 1993, Vol. 21, No.1, 145–150) was added dropwise to a solution of 3-carbamoyl-1,2-dihydro-3H-pyrrolo[3,2-e]indole-7-carboxylic acid (1.4 g, 6.1 mmol, D. L. Boger, R. S. Coleman, and B. J. Invergo. *J. Org. Chem.*, 1987, Vol.52, 1521–1530) and triethylamine (1.4 ml, 10 mmol) in 15 ml of anhydrous DMF. After 1 hr, the reaction mixture was concentrated under vacuum (0.2 mm).

The residue was triturated with 2 ml of dry dichloromethane. Ethyl ether (50 ml) was added and the mixture was left at 0° C. overnight. The precipitate was collected by filtration on sintered glass funnel, washed first with 50% ether/CH$_2$Cl$_2$ (10 ml), then with ether (50 ml) and dried in vacuo. The product was obtained as a yellow solid (1.8 g, 75%): $^1$H NMR (Me$_2$SO-d$_6$, 200 MHz, ppm) 12.32 (s, 1H, NH), 8.13 (d, 1H, J=9 Hz, C4-H), 8.01 (m, 1H, C$_6$F$_4$H), 7.41 (s, 1H, C8-H), 7.26 (d, 1H, J=9 Hz, C5-H), 6.17 (s, 2H, CONH$_2$), 3.99 (t, 2H, J=9 Hz, NCH$_2$CH$_2$), 3.30 (t, 2H, J=9 Hz, NCH$_2$CH$_2$). Anal. Calcd. for C$_{18}$H$_{11}$N$_3$O$_3$F$_4$×2H$_2$O: C, 50.3; H, 3.52; N, 9.7. Found: C, 50.81; H, 3.60; N, 9.95.

2,3,5,6-Tetrafluorophenyl 3-(tert-butyloxycarbonyl)-1,2-dihydro-3H-pyrrolo[3,2-e]indole-7-carboxylate (1b)

2,3,5,6-Tetrafluorophenyl trifluoroacetate (2.6 g, 10 mmol) was added dropwise to a solution of 3-(tert-butyloxycarbonyl)-1,2-dihydro-3H-pyrrolo[3,2-e]indole-7-carboxylic acid (1.0 g, 3.7 mmol, D. L. Boger, R. S. Coleman, and B. J. Invergo. *J. Org. Chem.*, 1987, Vol.52, 1521–1530) and triethylamine (1.5 ml, 10 mmol) in 10 ml of anhydrous CH$_2$Cl$_2$. After 4 hrs, CH$_2$Cl$_2$ was removed by evaporation at reduced pressure. Flash chromatography (4×20 cm, hexane-ethyl acetate, 1:2) afforded 1b as a yellow crystalline solid (1.25 g, 75%): $^1$H NMR (Me$_2$SO-d$_6$, 200 MHz, ppm) 12.39 (d, 1H, J=1.4 Hz, NH), 8.02 (m, 1H, C$_6$F$_4$H), 7.9 (br s, 1H, C4-H), 7.45 (d, 1H, J=1.4 Hz, C8-H), 7.33 (d, 1H, J=9 Hz, C5-H), 4.02 (t, 2H, J=9 Hz, NCH$_2$CH$_2$), 3.26 (t, 2H, J=9 Hz, NCH$_2$CH$_2$), 1.51 (s, 9H, C(CH$_3$)$_3$). Anal. Calcd. for C$_{22}$H$_{18}$N$_2$O$_4$F$_4$: C, 58.67; H, 4.03; N, 6.22. Found: C, 58.45; H, 4.09; N, 6.13.

3-carbamoyl-1,2-dihydro-3H-pyrrolo[3,2-e]indole-7-carboxylate dimer methyl ester (2a)

A solution of methyl 1,2-dihydro-3H-pyrroloindole-7-carboxylate (0.6 g, 1.5 mmol), 1a (0.45 g, 2.25 mmol) and triethylamine (0.2 ml, 1.4 mmol) in 10 ml of anhydrous DMF was incubated at RT for 24 hrs and then at 0° C. for 12 hrs. The resulting insoluble solid was collected by filtration, washed with DMF (10 ml) and ether (20 ml). Drying in vacuo afforded 2a (0.61 g, 91%) as a pale yellow solid: ($^1$H NMR (Me$_2$SO-d$_6$, 200 MHz, ppm) 12.00 (d, 1H, J=1.8 Hz, NH'), 11.54 (s, 1H, NH), 8.28 (d, 1H, J=9 Hz, C4'-H), 7.97 (d, 1H, J=9 Hz, C4-H), 7.33 (d, 1H, J=9 z, C5'-H), 7.22 (d, 1H, J=9 z, C5-H), 7.13 (d, 1H, J=1.4 Hz, C8'-H), 6.94 (d, 1H, J=1.1 Hz, C8-H), 6.01 (s, 2H, CONH$_2$), 4.62 (t, 2H, J=8 Hz, (NH$_2$CH$_2$)'), 3.98 (t, 2H, J=8 Hz, NCH$_2$CH$_2$), 3.88 (s, 3H, CH$_3$), 3.41 (t, 2H, J=8 Hz, (NCH$_2$CH$_2$)'), 3.29 (t, 2H, NCH$_2$CH$_2$, partially obscured by water). Anal. Calcd. for C$_{24}$H$_{21}$N$_5$O$_5$×1H$_2$O×1DMF: C, 58.69; H, 5.84; N, 15.21. Found: C, 58.93; H, 5.76; N, 15.82.

3-(tert-Butyloxycarbonyl)-1,2-dihydro-3H-pyrrolo[3,2-e]indole-7-carboxylate dimer methyl ester (2c)

A solution of methyl 1,2-dihydro-3H-pyrroloindole-7-carboxylate (0.5 g, 2.5 mmol), 1b (1.0 g, 2.2 mmol) and triethylamine (0.1 ml, 0.7 mmol) in 10 ml of anhydrous DMF was incubated at RT for 10 hrs and at 0° C. for 12 hrs. The resulting insoluble solid was collected by filtration, washed with DMF (5 ml) and ether (40 ml). Drying in vacuo afforded 2c (0.81 g, 74%) as an off-white solid: $^1$H NMR (Me$_2$SO-d$_6$, 200 MHz, ppm) 12.01 (s, 1H, NH'), 11.64 (s, 1H, NH), 8.28 (d, 1H, J=9 Hz, C4'-H), 7.8 (br s, 1H, C4-H), 7.32 (apparent t, 2H, C5'-H+C5-H), 7.13 (d, 1H, J=1.1 Hz, C8'-H), 6.98 (d, 1H, J=1.1 Hz, C8-H), 4.62 (t, 2H, J=8 Hz, (NH$_2$CH$_2$)'), 4.02 (t, 2H, J=8 Hz, NCH$_2$CH$_2$), 3.88 (s, 3H, CH$_3$), 3.41 (t, 2H, J=8 Hz, (NCH$_2$CH$_2$)'), 3.25 (t, 2H, NCH$_2$CH$_2$), 1.52 (s, 9H, C(CH$_3$)). Anal. Calcd. for C$_{28}$H$_{28}$N$_4$O$_5$: C, 67.19; H, 5.64; N, 11.19. Found: 66.72, H, 5.69; N, 11.31.

2,3,5,6-Tetrafluorophenyl 3-carbamoyl-1,2-dihydro-3H-pyrrolo[3,2-e]indole-7-carboxylate dimer (2e)

2,3,5,6-Tetrafluorophenyl trifluoroacetate (2.6 g, 10 mmol) was added dropwise to a suspension of 2b (1.2 g, 2.8 mmol, D. L. Boger, R. S. Coleman, and B. J. Invergo. *J. Org. Chem.*, 1987, Vol.52, 1521–1530) in 15 ml of anhydrous DMF. Triethylamine (1.4 ml, 10 mmol) was added and the mixture was stirred for 3 hrs. The mixture was concentrated in vacuo (0.2 mm) using rotary evaporator. The residue was triturated with 20 ml of dry dichloromethane. The product obtained was filtered, washed with dichloromethane (10 ml), ether (20 ml), and dried in vacuo to give 2e as a yellow solid (1.5 g, 93%): ($^1$H NMR (Me$_2$SO-d$_6$, 200 MHz, ppm) 12.51 (d, 1H, J=1.8 Hz, NH'), 11.58 (s, 1H, NH), 8.39 (d, 1H, J=8.9 Hz, C4'-H), 8.04 (m, 1H, C$_6$F$_4$H), 7.98 (d, 1H, J=8.8 Hz, C4-H), 7.58 (s, 1H, C8'), 7.42 (d, 1H, J=9 Hz, C5'-H), 7.22 (d, 1H, J=9 Hz, C5-H), 6.98 (s, 1H, C8-H), 6.11 (s, 2H, CONH$_2$), 4.66 (t, 2H, J=7.8 Hz, (NCH$_2$CH$_2$)'), 3.94 (t, 2H, J=9.1 Hz, NCH$_2$CH$_2$), 3.47 (t, 2H, J=8 Hz, (NCH$_2$CH$_2$)'), 3.29 (t, 2H, J=9.1 Hz, NCH$_2$CH$_2$). Anal. Cacld. for C$_{29}$H$_{19}$N$_5$O$_4$F$_4$×1.5H$_2$O: C, 57.62; H, 3.67; N, 11.59. Found: C, 57.18; H, 3.31; N, 11.54.

2,3,5,6-Tetrafluorophenyl 3-(tert-butyloxycarbonyl)-1,2-dihydro-3H-pyrrolo[3,2-e]indole-7-carboxylate dimer (2f)

2,3,5,6-Tetrafluorophenyl trifluoroacetate (0.75 g, 2.9 mmol) was added dropwise to a suspension of 2d (0.25 g, 0.5 mmol, D. L. Boger, R. S. Coleman, and B. J. Invergo. *J. Org. Chem.*, 1987, Vol.52, 1521–1530) and triethylamine (0.5 ml, 3.5 mmol) in a mixture of anhydrous CH$_2$Cl$_2$(8 ml) and DMF (2 ml). The mixture was stirred for 20 hrs. The resulting clear solution was concentrated in vacuo and was added dropwise to 40 ml of 1M sodium acetate (pH 7.5). The precipitate was centrifuged, washed with water (2×40 ml), with 10% MeOH in ether(2×40 ml), with ether (40 ml), and with hexane (40 ml). Finally it was dried in vacuo to give 2f as a pale yellow solid (0.29 g, 91%): ($^1$H NMR (Me$_2$SO-d$_6$, 200 MHz, ppm) 12.51 (s, 1H, NH'), 11.66 (s, 1H, NH), 8.37 (d, 1H, J=8.8 Hz, C4'-H), 8.03 (m, 1H, C$_6$F$_4$H), 7.8 (br s, 1H, C4-H), 7.58 (s, 1H, C8'-H), 7.40 (d, 1H, J=9.1 Hz, C5'-H), 7.27 (d, 1H, J=8.6 Hz, C5-H), 7.1 (s, 1H, C8-H), 4.65 (t, 2H, J=8 Hz, (NCH$_2$CH$_2$)'), 4.02 (t, 2H, J=9 Hz, NCH$_2$CH$_2$), 3.46 (t, 2H, J=8 Hz, (NCH$_2$CH$_2$)'), 3.25 (t, 2H, J=8.9 Hz, NCH$_2$CH$_2$), 1.51 (s, 9H, C(CH$_3$)$_3$). Anal. Calcd. for C$_{33}$H$_{26}$N$_4$O$_5$F$_4$×0.5H$_2$O: C, 61.59; H, 4.23; N, 8.71. Found: C, 61.73; H, 4.12; N, 8.61.

3-carbamoyl-1,2-dihydro-3H-pyrrolo[3,2-e]indole-7-carboxylate trimer methyl ester (3a)

A solution of methyl 1,2-dihydro-3H-pyrroloindole-7-carboxylate (1.0 g, 5 mmol), 2e (1.2 g, 2.1 mmol) and triethylamine (0.1 ml, mmol) in 15 ml of anhydrous DMF was incubated at RT for 24 hrs and at 0° C. for 12 hrs. The resulting insoluble solid was collected by filtration, washed with DMF (10 ml), CH$_2$Cl$_2$ (20 ml) and ether (20 ml). Drying in vacuo afforded 3a (1.1 g, 83%) as a pale yellow solid: ($^1$H NMR (Me$_2$SO-d$_6$, 200 MHz, ppm) 12.02 (s, 1H, NH"), 11.75 (s, 1H, NH'), 11.56 (s, 1H, NH), 8.28 (apparent t, 2H, J=8.3 Hz, C4-H"+C4'-H), 7.98 (d, 1H, J=9.4 Hz, C4-H), 7.98 (d, 1H, J=9 Hz, C4-H), 7.39–7.33 (2 d, 2H, C5"-H+C5'-H), 7.23 (d, 1H, J=8.7 Hz, C5-H), 7.14 (d, 1H, J=1.6 Hz, C8"-H), 7.10 (d, 1H, J=1 Hz, C8'-H), 6.97 (s, 1H, C8-H), 6.11 (s, 2H, CONH$_2$), 4.65 (t, 4H, (NCH$_2$CH$_2$)"+ (NCH$_2$CH$_2$)'), 3.98 (t, 2H, J=8.7 Hz, NCH$_2$CH$_2$), 3.88 (s, 3H, CH$_3$), 3.48–3.25 (m, 6H, (NCH$_2$CH$_2$)"+(NCH$_2$CH$_2$)'+NCH$_2$CH$_2$ partially obscured with H$_2$O). Anal. Calcd. for C$_{35}$H$_{29}$N$_7$O$_5$×4.5H$_2$O: C, 59.32; H, 5.0; N, 13.03. Found: C, 58.9; N, 5.06; N, 13.77.

2,3,5,6-Tetrafluorophenyl 3-carbamoyl-1,2-dihydro-3H-pyrrolo[3,2-e]indole-7-carboxylate trimer (3c)

2,3,5,6-Tetrafluorophenyltrifluoroacetate (2.6 g, 10 mmol) was added dropwise to a suspension of 3b (1.1 g, 1.8 mmol) in 15 ml of anhydrous DMF and triethylamine (1.4 ml, 10 mmol). The mixture was stirred for 3 hrs. The mixture was concentrated in vacuo (0.2 mm). The residue was triturated with a mixture of dry dichloromethane (20 ml) and methanol (2 ml). The resulting product was collected by filtration, washed with dichloromethane (20 ml), ether (20 ml), and dried in vacuo to give 1.3 g (95%) of a yellow-green solid: ($^1$H NMR (Me$_2$SO-d$_6$, 200 MHz, ppm) 12.54 (d, 1H, J=1 Hz, NH"), 11.79 (s, 1H, NH'), 11.56 (s, 1H, NH), 8.41 (d, 1H, J=9.3 Hz, C4-H"), 8.27 (d, 1H, J=9.4 Hz, C4'-H), 8.03 (m, 1H, C$_6$F$_4$H), 7.98 (d, 1H, J=9 Hz, C4-H), 7.56 (s, 1H, C8"-H), 7.45–7.35 (m, 2H, C5"-H+C5'-H), 7.23 (d, 1H, J=9.2 Hz, C5-H), 7.13 (s, 1H, C8'-H), 6.97 (s, 1H, C8-H), 6.11 (s, 2H, CONH$_2$), 4.65 (m, 4H, (NCH$_2$CH$_2$)"+ (NCH$_2$CH$_2$)'), 3.98 (t, 2H, J=8.7 Hz, NCH$_2$CH$_2$), 3.45 (m, 4H, (NCH$_2$CH$_2$)"+(NCH$_2$CH$_2$)'), 3.25 (t, 2H, J=8.7 Hz, NCH$_2$CH$_2$). Anal. Calcd. for C$_{40}$H$_{27}$N$_7$O$_5$F$_4$×2H$_2$O: C, 61.59; H, 4.23; N, 8.71. Found: C, 61.73; H, 4.12; N, 8.61.

[3-carbamoyl-1,2-dihydro-3H-pyrrolo[3,2-e]indole-7-carbox]- 1-amido-3-propanol trimer (3d)

A solution of 3-amino-1-propanol (70 µl, 1.4 mmol), 3c (75 mg, 0.1 mmol) and triethylamine (0.1 ml, mmol) in 2.5 ml of anhydrous DMF was stirred at RT for 10 hrs. The resulting insoluble solid was collected by filtration, washed with DMF (2 ml), CH$_2$Cl$_2$ (10 ml) and ether (20 ml). Drying in vacuo afforded 3d (55 mg, 89%) as a pale yellow solid: ($^1$H NMR (Me$_2$SO-d$_6$, 200 MHz, ppm) 11.76 (s, 1H, NH"), 11.65 (s, 1H, NH'), 11.57 (s, 1H, NH), 8.47 (m, 1H, C4-H), 8.24 (m, 1H, C4-H), 7.99 (d, 1H, J=8.4 Hz, C4-H), 7.40–7.32 (2d, 2H, C5"-H+C5'-H), 7.23 (d, 1H, J=8.9 Hz, C5-H), 7.12 (s, 1H, C8"-H), 7.10 (s, 1H, C8'-H), 6.99 (s, 1H, C8-H), 6.12 (s, 3H, CONH$_2$+NHCO), 4.66 (t, 4H, (NCH$_2$CH$_2$)"+(NCH$_2$CH$_2$)'), 3.98 (t, 2H, J=8.7 Hz, NCH$_2$CH$_2$), 3.51–3.25 (m, 10H, (NCH$_2$CH$_2$)"+(NCH$_2$CH$_2$)'+NCH$_2$CH$_2$+NHCH$_2$+CH$_2$OH partially obscured with H$_2$O), 1.70 (p, 2H, J=6.6 Hz, CH$_2$CH$_2$CH$_2$).

2,3,5,6-Tetrafluorophenyl 3-[N-(9-fluorenylmethoxycarbonyl)]aminopropionate (4)

2,3,5,6-Tetrafluorophenyl trifluoroacetate (1.7 g, 6.5 mmol) was added dropwise to a solution of FMOC-alanine (2.0 g, 6.4 mmol) and triethylamine (1.0 ml, 7 mmol) in 20 ml of anhydrous CH$_2$Cl$_2$. After 1 hr, CH$_2$Cl$_2$ was removed by evaporation at reduced pressure using rotary evaporator, redissolved in 30 ml ethylacetate/hexane (1:1). Flash chromatography (4×20 cm, hexane/ethyl acetate, 3:1) afforded rude 4 as a white solid. It was recrystallized from hexane/ethyl acetate to give 4 as a white crystalline solid (2.3 g, 78%): $^1$H NMR (CDCl$_3$, 200 MHz, ppm) 7.73 (d, 2H, J=7.1 Hz, aromatic protons), 7.75 (d, 2H, J=7.7 Hz, aromatic protons), 7.24–7.42 (m, 4H, aromatic protons), 7.01 (m, 1H, $C_6F_4H$), 5.21 (br s, 1H, —CONH—), 4.38 (d, 2H, J=7.1 Hz, —CH$_2$OCO—), 4.20 (m, 1H, benzyl proton), 3.58 (m, 2H, NCH$_2$), 2.93 (t, 2H, J=5.4 Hz, —CH$_2$CO—). Anal. Calcd. for $C_{24}H_{17}NO_4F_4$: C, 62.75; H, 3.73; N, 3.05. Found: C, 62.52; H, 3.59; N, 3.01.

1-[3-|N-(9-Fluorenylmethoxycarbonyl)amino|-1-oxopropyl|amino-(R,S)-2,3-propanediol (5)

A solution of 4 (2.0 g, 4.35 mmol) in 20 ml of anhydrous CH$_2$Cl$_2$ was added to a stirred solution of 3-amino-1,2-propanediol (0.6, mmol) in 10 ml MeOH. After 10 min, acetic acid (3 ml) was added and the mixture was evaporated to dryness. The residue was triturated with 100 ml of water. The obtained solid was filtered off, washed with water and dried by co-evaporation with toluene (2×50 ml) at reduced pressure. Washing with 50 ml of ethyl acetate followed by drying in vacuo overnight yielded 5 as a white crystalline solid (1.65 g, 99%): $^1$H NMR (CDCl$_3$+MeOD-d4, 200 MHz, ppm, Me$_4$Si) 7.77 (d, 2H, J=7.7 Hz, aromatic protons), 7.61 (d, 2H, J=7.3 Hz, aromatic protons), 7.45–7.29 (m, 4H, aromatic protons), 4.35 (d, 2H, J=7.1 Hz, —CH$_2$OCO—), 4.22 (m, 1H, benzyl proton), 3.72 (m, 1H, —CH— from NHCH$_2$CHOHCH$_2$OH), 3.52–3.27 (m, 6H, OCONHC H$_2$+CH$_2$CHOHCH$_2$OH), 2.44 (t, 2H, J=6.6 Hz, —CH$_2$CO—); Anal. Calcd. for $C_{21}H_{24}N_2O_5$: C, 5.61; H, 6.29; N, 7.29%. Found: C, 65.43; H, 6.28; N, 7.21.

1-3-[N-(9-Fluorenylmethoxycarbonyl)amino]-1-oxopropyl]amino-(R,S)-2-|[bis(methoxyphenyl)phenylmethoxy]metyl]-2-ethanol (6)

To a stirred solution of 5 (1.6 g, 4.2 mmol) in 30 ml of anhydrous pyridine was added DMTrCl (1.6 g, 4.7 mm ol ). After stirring for 3 hrs under argon, the mixture was evaporated to dryness. Residual pyridine was removed by co-evaporation with toluene. The residue was dissolved in 100 ml of CH$_2$Cl$_2$, washed with 2×100 ml water, dried over sodium sulfate, and evaporated to dryness. The residue was purified by flash chromatography (4×20 cm, silica) using ethyl acetate as an eluent. The fractions containing pure product were combined and evaporated to dryness to yield 1.9 g (66%) of 6 as a colorless foam: $^1$H NMR (CDCl$_3$, 200 MHz, ppm, Me$_4$Si) 7.72 (d, 2H, J=7.2 Hz, aromatic protons), 7.56 (d, 2H, J=7 Hz, aromatic protons), 7.40–7.20 (m, 13H, aromatic protons), 6.80 (d, 4H, J=9 Hz, DMTr protons), 5.76 (br s, 1H, NH), 5.42 (br s, 1H, NH), 4.35 (d, 2H, J=6.6 Hz, —CH$_2$OCO—), 4.17 (m, 1H, benzyl proton), 3.83 (m, 1H, —CH— from NHCH$_2$CHOHCH$_2$OH), 3.75 (s, 6H, OCH$_3$), 3.60–3.30 (m, 4H, OCONHCH$_2$+C H$_2$CHOHCH$_2$OH), 3.13 (d, 2H, J=5.4 Hz, CH$_2$ODMTr), 2.30 (t, 2H, J=5.4 Hz, —CH$_2$CO—); Anal. Calcd. for $C_{42}H_{42}N_2O_7$: C, 73.45; H, 6.16; N, 4.08. Found: C, 65.43; H, 6.28; N, 7.21.

2,3,5,6-Tetrafluorophenyl 1-[3-[N-(9-fluorenylmethoxycarbonyl) amino]-1-oxopropyl] amino-(R,S)-2-|[bis(methoxyphenyl) phenylmethoxy]metyl]-2-ethyl butanedioate (7)

To a solution of 6 (1.2 g, 1.75 mmol), triethylamine (0.2 g, 2 mmol), 1-methylimidazole (20 μl) in 10 ml of anhydrous CH$_2$Cl$_2$ was added 0.2 g (2 mmol) of succinic anhydride. This solution was stirred for 20 hrs. Triethylamine (60 μl) was added to the solution followed by 0.6 g (2.2 mmol) of 2,3,5,6-tetrafluorophenyl trifluoroacetate. After 1 hr, CH$_2$Cl$_2$ was removed by evaporation at reduced pressure using a rotary evaporator, and the residue was dissolved in 15 ml ethylacetate/hexane (1:2). Flash chromatography (4×20 cm, hexane/ethyl acetate, 2:1) afforded 1b as a pale yellow foam (1.2 g, 73%): $^1$H NMR (CDCl$_3$, 300 MHz, ppm, Me$_4$Si) 7.71 (d, 2H, J=7.2 Hz, aromatic protons), 7.54 (d, 2H, J=7 Hz, aromatic protons), 7.40–7.20 (m, 13H, aromatic protons), 7.00 (m, 1H, C$_6$F$_4$H), 6.78 (d, 4H, J=7 Hz, DMTr protons), 5.71 (br s, 1H, NH), 5.42 (br s, 1H, NH), 5.15 (m, 1H, —CH— from NHCH$_2$CHOHCH$_2$OH), 4.31 (d, 2H, J=6.2 Hz, —CH$_2$OCO—), 4.16 (d, 5.5 Hz, 1H, benzyl proton), 3.74 (s, 6H, OCH$_3$), 3.60–3.30 (m, 4H, OCONHCH$_2$+C H$_2$CHOHCH$_2$OH), 3.20 (br s, 2H, CH$_2$ODMTr), 2.98 (br s, 2H, COCH$_2$CH$_2$CO), 2.72 (br s, 2H, COCH$_2$CH$_2$CO), 2.20 (br s, 2H, —CH$_2$CO—); Anal. Calcd. for $C_{42}H_{42}N_2O_7$: C, 66.80; H, 4.96; N, 3.00. Found: C, 66.18; H, 4.98; N, 2.86.

Preparation of CPG derivative 8

A mixture of 5.0 g of long chain aminoalkyl controlled pore glass (LCAA-CPG), 0.5 ml of 1-methylimidazole, and 0.45 g (0.5 mmol) of 7 in 20 ml of anhydrous pyridine was swirled in 100 ml flask (orbital mixer, 150 rpm). After 3 hrs, the CPG was filtered on a sintered glass funnel and washed with 100 ml portions of DMF, acetone, and diethyl ether. The CPG was dried in vacuo and treated with a mixture of pyridine (20 ml), acetic anhydride (2 ml), and 1-methylimidazole (2 ml). After swirling for 30 min, the CPG was washed with pyridine, methanol, and diethyl ether, then dried in vacuo. The product (8) was analyzed for dimethoxytrityl (DMTr) content according to the literature method (T. Atkinson and M. Smith, in M. Gait (ed.), Oligonucleotide Synthesis. A Practical Approach. IRL Press, 1984, Oxford, UK, pp.35–81) and found to have a loading of 28 μmol/g.

Preparation of CPG derivative 9

The CPG derivative 8 (3.0 g) was treated twice with 20 ml of 20% piperidine in dry DMF for 5 min each time. The CPG was washed with 100 ml portions of DMF, methanol, and diethyl ether, then dried in vacuo.

Preparation of CPG derivative 10

A mixture of 2.5 g of 9, 7.5 ml of triethylamine, and 0.38 g (0.5 mmol) of 3c in 7.5 ml of anhydrous DMSO was swirled in 50 ml flask (orbital mixer, 150 funnel rpm). After 2 days, the CPG was filtered on a sintered glass funnel and washed with 100 ml portions of DMSO, acetone, and diethyl ether. The CPG was dried in vacuo and treated with a mixture of pyridine (10 ml), acetic anhydride (1 ml), and 1-methylimidazole (1 ml). After swirling for 30 min, the CPG was washed with DMSO, pyridine, methanol, and diethyl ether, then dried in vacuo.

2-[4-(Phenylazo)benzylthio]ethyl 5-[(tert-butyloxy) carboxamido]pentylcarboxylate (11)

6-[(Tert-butyloxy) carboxamido]hexanoic acid (4.16 g, 18 mmol) was dried by co-evaporation with dry DMF (70° C.). The residue was redissolved in dry DMF (25 mL) and 2-[4-(phenylazo)-benzylthio]-ethanol (4.08 g, 15 mmol), N,N'-dicyclohexyl carbodiimide (3.71 g, 18 mmol), 4-dimethylaminopyridine (1.83 g, 15 mmol) were added at 0° C. After stirring at 0° C. for 2 h and 20° C. for 12 h, the reaction mixture was evaporated to dryness by co-evaporation with butyl acetate, and additional ethyl acetate (150 mL) was added. This solution was extracted with 0.7M HCl (1×30 mL), 5% NaHCO$_3$ and H$_2$O (2×50 mL). The organic layer was dried over Na$_2$SO$_4$ and concentrated with rotary evaporator. Washing with 20 mL of ether and filtration afforded compound 11 (6.91 g, 89%). $^1$H NMR (CDCl$_3$, 200 MHz, ppm): 7.91 (m, 4H), 7.52 (m, 5H), 4.48 (t, 2H), 4.34 (s, 2H), 3.20 (t, 2H), 3.08 (m, 2H), 2.35 (t, 2H), 1.64–1.2 (m, 7H), 1.41 (s, 9H).

1,2,3-benzotriazol-1-yl 1-methyl-4-(tert-butyloxy) carboxamido-pyrrole-2-carboxylate N,N'-Dicyclohexylcarbodiimide (1.1 g, 5.3 mmol) was added to a solution of 1-methyl-4-[tert-butyloxy) carboxamido|pyrrole-2-carboxylic acid[4] (1.2 g, 5.2 mmol) and 1-hydroxybenzotriazol (0.63 g, 4.7 mmol). After stirring for 1 hr, the mixture was filtered through the sintered glass filter to separate precipitated N,N'-dicyclohexylcarbodiimide. The filtrate was evaporated to dryness, redissolved in a mixture of CHCl$_3$ and pentane (1:1), and loaded onto a silica gel column. The fractions containing pure product were combined and evaporated to dryness to give 1.45 g (80%) of the desired product as a white solid: mp=138°–138.5° C.; $^1$H NMR (CDCl$_3$, 200 MHz) 8.04 (d, 1H), 7.49–7.40 (m, 4H), 7.09 (d, 1H), 3.87 (s, 3H), 1.50 (s, 9H).

2-[4-(Phenylazo)benzylthio]ethyl 5-[1-methyl-4-(tert-butyloxy)carboxamido|pyrrole-2-carboxamido] pentylcarboxylate (12)

Trifluoroacetic acid (5 mL) was added at 0° C. to 11 (0.73 g, 1.5 mmol). After stirring at 0° C. for 20 min the reaction mixture was evaporated to dryness by co-evaporation with CHCl$_3$. The residue was dissolved in dry CH$_2$Cl$_2$ (15 mL) and 1,2,3-benzotriazol-1-yl 1-methyl-4-(tert-butyloxy) carboxamido-pyrrole-2-carboxylate (0.59 g, 1.65 mmol), dry triethylamine (0.23 g, 2.3 mmol) were added. After stirring at ambient temperature for 15 min, CHCl$_3$ was added (100 mL). The reaction mixture was extracted with 5% NaHCO$_3$ (2×20 mL), H$_2$O(2×20 mL). The organic layer was dried over Na$_2$SO$_4$ and concentrated on a rotary evaporator. Chromatography on silica gel (100 g) with CHCl$_3$ afforded 0.88 g (91.8%) 12. $^1$H NMR (CDCl$_3$, 200 MHz, ppm): 7.88 (m, 4H), 7.46 (m, 5H), 6.74 (s, 1H), 6.38 (s, 1H), 6.26 (s, 1H), 5.87 (t, 1H), 4.18 (t, 2H, J=6 Hz), 3.82 (s, 3H), 3.79 (s, 2H), 3.3 (m, 2H), 2.63 (t, 2H, J=6 Hz), 2.30 (t, 2H, J=6 Hz), 1.64–1.2 (m, 6H), 1.46 (s, 9H).

2-[4-(Phenylazo)benzylthio]ethyl 5-[1-methyl-4-[1-methyl-4- (tert-butyloxy)carboxamidopyrrole-2-carboxamido|pyrrole-2- carboxamido] pentylcarboxylate (13)

A solution of 12 (2.43 g, 4 mmol) in dry CH$_2$Cl$_2$ (8 mL) was treated with trifluoroacetic acid (4 mL) at 0° C. The resulting solution was left at ambient temperature in stopped flask for 1 h and then partitioned between 30% aqueous K$_2$CO$_3$ (30 mL) and CH$_2$Cl$_2$ (30 mL). The lower layer was collected. The aqueous phase was extracted with dichloromethane (2×20 mL), and the combined organic extracts, after being washed with H$_2$O(1×20 mL), were dried over Na$_2$SO$_4$ and evaporated. The residue was dissolved in CH$_2$Cl$_2$ (10 mL) and 1,2,3-benzotriazol-1-yl 1-methyl-4-(tert- butyloxy) carboxamidopyrrole-2-carboxylate (1.43 g, 4 mmol) and dry triethylamine (0.8 g, 8 mmol) were added. After stirring at ambient temperature for 30 min, CHCl$_3$ (100 mL) was added. The reaction mixture was extracted with 5% NaHCO$_3$ (2×20 mL), H$_2$O(2×20 mL). The organic layer was dried over Na$_2$SO$_4$ and concentrated on a rotary evaporator. Chromatography on silica gel (100 g) with CHCl$_3$ afforded 1.95 g (66.8%) of 13. $^1$H NMR (CDCl$_3$, 200 MHz, ppm): 7.87 (m, 4H), 7.46 (m, 5H), 7.04 (d, 1H, J=1.5 Hz), 6.77 (br s, 1H), 6.52 (br s, 1H), 6.50 (d, 1H, J=1.5 Hz), 6.31 (br s, 1H), 5.95 (t, 1H), 4.19 (t, 2H, J=6 Hz), 3.85 (s, 6H), 3.78 (s, 2H), 3.32 (m, 2H), 2.64 (t, 2H, J=6 Hz), 2.31 (t, 2H, J=6 Hz), 1.64–1.2 (m, 6H), 1.48 (s, 9H).

2-[4-(Phenylazo)benzylthio]ethyl 5-[1-methyl-4-[1-methyl-4-[1-methyl-4-(tert-butyloxy) carboxamidopyrrole-2-carboxamido|pyrrole-2-carboxamido|pyrrole-2-carboxamido] pentylcarboxylate (14)

A solution of 13 (1.90 g, 2.6 mmol) in dry CH$_2$Cl$_2$ (6 mL) was treated with trifluoroacetic acid (3 mL) at 0° C. The resulting solution was left at ambient temperature in stopped flask for 1 h and then partitioned between 30% aqueous K$_2$CO$_3$ (30 mL) and CH$_2$Cl$_2$ (30 mL). The lower layer was collected. The aqueous phase was extracted with dichloromethane (2×20 mL), and the combined organic extracts, after being washed with H$_2$O (1×20 mL), were dried over Na$_2$SO$_4$ and evaporated. The residue was dissolved in CH$_2$Cl$_2$ (2.5 mL) and 1,2,3-benzotriazol-1-yl 1-methyl-4-(tert-butyloxy) carboxamidopyrrole-2-carboxylate (1.4 g, 3.9 mmol), dry triethylamine (0.8 g, 8 mmol) were added. After stirring at ambient temperature for 1 h, CHCl$_3$ (100 mL) was added. The reaction mixture was extracted with 5% NaHCO$_3$ (2×20 mL), H$_2$O (2×20 mL). The organic layer was dried over Na$_2$SO$_4$ and concentrated on a rotary evaporator. Chromatography on silica gel (100 g) with 0–1.5% methanol in CHCl$_3$ afforded 1.56 g (70.5%) of 14. $^1$H NMR (CDCl$_3$, 200 MHz, ppm): 7.87 (m, 4H), 7.68 (br s, 1H), 7.60 (br s, 1H), 7.46 (m, 5H), 7.08 (br s, 2H), 6.78 (br s, 1H), 6.56 (d, 1H, J=1.5 Hz), 6.60 (br s, 1H), 6.55 (d, 1H, J=1.5 Hz), 6.03 (t, 1H), 4.18 (t, 2H, J=6 Hz), 3.86 (m, 9H), 3.78 (s, 2H), 3.32 (m, 2H), 2.63 (t, 2H, J=6 Hz), 2.30 (t, 2H, J=6 Hz), 1.64–1.2 (m, 6H), 1.48 (s, 9H).

2-[4-(Phenylazo benzylthio]ethyl-5-[1-methyl-4-[1-methyl-4- [1-methyl-4-[1-methyl-4-(tert-butyloxy) carboxamidopyrrole-2-carboxamido|pyrrole-2-carboxamido|pyrrole-2-carboxamido|pyrrole-2-carboxamido]pentylcarboxylate (15)

A solution of 14 (0.32 g, 0.32 mmol) in dry CH$_2$Cl$_2$ (5 mL) was treated with trifluoroacetic acid (2.5 mL) at 0° C. The resulting solution was left at ambient temperature in stopped flask for 1 h and then partitioned between 30% aqueous K$_2$CO$_3$ (30 mL) and CH$_2$Cl$_2$ (30 mL). The lower layer was collected. The aqueous phase was extracted with dichloromethane (2×20 mL), and the combined organic extracts, after being washed with H$_2$O (1×20 mL), were dried over Na$_2$SO$_4$ and evaporated. The residue was dissolved in CH$_2$Cl$_2$ (1 mL) and 1,2,3-benzotriazol-1-yl 1-methyl-4-(tert- butyloxy)carboxamidopyrrole-2-carboxylate (0.11 g, 0.32 mmol), dry triethylamine (0.06 g, 0.03 mmol) were added. After stirring at ambient temperature for 1.5 h, CHCl$_3$ (100 mL) was added. The suspension was filtered and the filtrate was extracted with 5% NaHCO$_3$ (2×20 mL), H$_2$O (2×20 mL). The organic layer was dried over Na$_2$SO$_4$ and evaporated to dryness. The yield of 15 was 0.25 g (80%). $^1$H NMR (CDCl$_3$, 200 MHz, ppm): 8.17 (br s, 1H), 7.98 (br s,), 7.96 (br s,), 1H 7.85 (m, 4H), 7.44 (m, 5H), 7.09 (br s, 2H), 7.02 (s, 1H), 6.78 (br s, 1H), 6.74 (br s, 1H), 6.66 (s, 1H), 6.58 (s, 3H), 6.29 (t, 1H), 4.18 (t, 2H, J=6 Hz), 3.78 (m, 14H), 3.28 (m, 2H), 2.60 (t, 2H, J=6 Hz), 2.26 (t, 2H, J=6 Hz), 1.64–1.2 (m, 6H), 1.48 (s, 9H).

2-[4-(Phenylazo)benzylthio]ethyl 5-[1-methyl-4-[1-methyl-4-[1-methyl-4-[1-methyl-4-[1-methyl-4-(tert-butyloxy) carboxamido|pyrrole-2-carboxamido] pyrrole-2-carboxamido|pyrrole-2-carboxamido] pyrrole-2-carboxamido|pyrrole-2-carboxamido] pentylcarboxylate (16)

A solution of 15 (0.65 g, 0.67 mmol) in dry CH$_2$Cl$_2$ (10 mL) was treated with trifluoroacetic acid (5 mL) at 0° C. The resulting yellowish solution was left at ambient temperature in stopped flask for 1 h and then partitioned between 30% aqueous K$_2$CO$_3$ (30 mL) and CH$_2$Cl$_2$ (30 mL). The lower layer was collected. The aqueous phase was extracted with dichloromethane (2×20 mL), and the combined organic extracts, after being washed with H$_2$O (1×20 mL), were dried over Na$_2$SO$_4$ and evaporated. The residue was dissolved in DMF (1 mL) and 1,2,3-benzotriazol-1-yl 1-methyl-4-(tert-butyloxy)carboxamidopyrrole-2-carboxylate (0.24 g, 0.67 mmol), dry triethylamine (0.13 g, 0.67 mmol) were added. After stirring at ambient temperature for 3 h, the reaction mixture was evaporated to dryness by co-evaporation with butyl acetate. The residue was dissolved in 3 mL 2.5% DMF in CHCl$_3$. Chromatography on silica gel (100 g) with 0–2.5% methanol in CHCl$_3$ (2.5% DMF) afforded 0.67 g (45%) of 16.

2,3,5,6-Tetrafluorophenyl-4'-[bis(2-chloroethyl) amino]phenylbutyrate (Chlorambucil 2,3,5,6-tetrafluorophenyl ester)

To a solution of 0.25 g (0.82 mmol) of chlorambucil (supplied by Fluka A. G.), 0.3 g (1.1 mmol) of 2,3,5,6-tetrafluorophenyl trifluoroacetate in 5 ml of dry dichloromethane was added 0.2 Ml of dry triethylamine. The mixture was stirred under argon at room temperature for 0.5 h and evaporated. The residual oil was purified by column chromatography on silica gel with hexane-chloroform (2:1) as the eluting solvent to give the ester as an oil: 0.28 g (75%); TLC on silica gel (CHCl$_3$) R$_f$ 0.6; IR (in CHCl$_3$) 3010, 1780, 1613, 1521, 1485 cm$^{-1}$.

Introduction of chlorambucil residue into the primary amino groups of oligonucleotides Preparation of the cetyltrimethylammonium salt of oligonucleotides: a 100 µL of aqueous solution of oligonucleotide (50–500 ug), generally triethylammonium salt, was injected to a column packed with Dowex 50wx8 in the cetyltrimethylammonium form and prewashed with 50% alcohol in water. The column was eluted by 50% aqueous ethanol (0.1 mL/min). Oligonucleotide containing fraction was dried on a Speedvac over 2 hours and used in following reactions.

Ethanol solution (50 uL) of cetyltrimethylammonium salt of an oligonucleotide (50—100 µg) was mixed with of 0.08M solution of 2,3,5,6-tetrafluorophenyl-4'-[bis (2-chloroethyl)amino]phenylbutyrate (tetrafluorophenyl ester of chlorambucil) in acetonitrile (50 µL) and 3 µL of diisopropylethylamine. After shaking for three hours at room temperature, the product was precipitated by 2% LiClO$_4$ in acetone (1.5 mL). The product was reprecipitated from water (60 uL) by 2% LiClO$_4$ in acetone three times. Finally chlorambucil derivative of oligonucleotide was purified by Reverse Phase Chromatography with approximately 50–80% yield. The fraction containing a product was concentrated by approximately butanol. Isolated chlorambucil derivative of oligonucleotide was precipitated in acetone solution of LiClO$_4$, washed by acetone and dried under vacuum of oil pump. All manipulation of reactive oligonucleotide was performed as quickly as possible, with the product in ice-cold solution, starting from the chromatographic fraction collected.

Oligonucleotide synthesis

All oligonucleotides were prepared from 1 µmol of the appropriate CPG support on an ABM 394 using protocol supplied by manufacturer. Standard reagents for the -cyanoethylphosphoramidite coupling chemistry were purchased from Glen Research. 5'-aminohexyl modifications were introduced using an N-MMT-hexanolamine phosphoramidite linker (Glen Research). 3'-aminohexyl modifications were introduced using the CPG prepared as previously described, C. R. Petrie, M. W. Reed, A. D. Adams, and R. B. Meyer, Jr. *Bioconjugate Chemistry*, 1992, 3, 85–87.

Preparation of Conjugates (Reaction Scheme 3)

To a solution of cetyltrimethylammonium salt of an aminohexyl modified oligonucleotide (30–50 nmol, Jost, J.-P., Jiricny, J., and Saluz, H. (1989) Quantitative precipitation of short oligonucleotides with low concentrations of cetyltrimethylammonium bromide. *Nucleic Acids Res.* 17, 2143) and 1.5 µl of N,N-diisopropylethylamine in 40 µl of dry DMSO was added 40 µA of 4 mM solution of the TFP ester (1a, 1b, 2e, 2f or 3c). The reaction mixture was kept for 12 hrs at RT. The oligonucleotide related material was precipitated by addition of 1.5 ml of 2% LiClO$_4$ in acetone. The pellet was washed with acetone, and dried in vacuo. The pellet was redissolved in 60 µl of 50% DMF in H$_2$O and precipitated again as described above using 2% solution of LiClO$_4$ in acetone. This procedure was repeated twice. The residue was purified by HPLC (4.6×250 mm, C-18, Dynamax-300A, Rainin) using a gradient of acetonitrile from 20 to 75% in the presence of 50 mM LiClO$_4$. The fraction containing pure product was dried in vacuo using speedvac. The residue was dissolved in 60–80 µl of H$_2$O and precipitated with 1.5 ml of 2% LiClO$_4$ in acetone. After washing with acetone (2×1.5 ml) and drying in vacuo, the pellet was dissolved in 100 µl of H$_2$O. The yield of final product was 20–50%.

A modified procedure of Godovikova et al. (T. S. Godovikova, V. F. Zarytova, T. V. Maltzeva, L. M. Khalimskaya. *Bioorgan. Khim.*, 1989, 15, 1246–1259) was used for the preparation of the oligonucleotide conjugates bearing 4-amino-N-methylpyrrol-2-carboxylic acid residues. A solution of cetyltrimethylammonium salt of 3'-phosphate-containing oligonucleotide (50–100 nmol), triphenylphospine (10 mg), 2,2'-dipyridyldisulfide (10 mg), N,N-dimethylaminopyridine (10 mg), and one of the analogues selected from compounds 11 through 16 in 100 µl of dry DMF was incubated for 20 min at RT. The oligonucleotide related material was precipitated by addition of 1.5 ml of 2% LiClO$_4$ in acetone. The pellet was washed with acetone, and dried in vacuo. The residue was purified by HPLC using gradient of acetonitrile from 20 to 75% in presence of 50 mM LiClO$_4$. The fraction containing pure product was dried in vacuo using speedvac. The residue was dissolved in 60–80 µl of H$_2$O and precipitated with 1.5 ml of 2% LiClO$_4$ in acetone. After washing with acetone (2×1.5 ml) and drying in vacuo, the pellet was dissolved in 100 µl of H$_2$O. The yield of final product was 30–50%.

Preparation of Conjugates (Reaction Scheme 4)

CPG containing 5'-aminohexyl derivatized oligonucleotide obtained in a synthesis on 1 µmol scale was treated with 2% dichloroacetic acid in CH$_2$Cl$_2$ to remove the 9-fluorenylmethoxycarbonyl (Fmoc) protecting group from the amino group followed by washing with acetonitrile, and drying by flushing with argon. The CPG was transferred into 1.5 ml plastic tube and 100 ul of 50 mM solution of TFP ester in anhydrous DMSO was added. The tube was shaken for 24 hrs, then washed with 3×1.5 ml DMSO, 2×1.5 ml acetone, and dried in vacuo. The CPG was treated with concentrated ammonia to deprotect oligonucleotide using standard conditions. The resulting reaction mixture was separated using reverse phase HPLC as described above. Typical yield was about 50%.

Thermal Denaturation Studies

Optical melting curves of oligonucleotide complexes bearing 4-amino-N-methylpyrrol-2-carboxylic acid residues were obtained in 200 mM NaCl, 10 mM $Na_2HPO_4$, 0.1 mM EDTA (pH 7.0) on the UV detector of a Milichrom liquid chromatograph in a thermoregulated cell specially designed for this purpose. The data were collected and processed on a personal computer as described by S. G. Lokhov et al. (S. G. Lokhov, M. A. Podyminogin, D. S. Sergeev, V. N. Silnikov, I. V. Kutyavin, G. V. Shishkin, V. F. Zarytova, *Bioconjugate Chem.* 1992, 3, 414).

The oligonucleotide complexes carrying 1,2-dihydro-3H-pyrrolo[3,2-e]indole-7-carboxylic acid (CDPI) residues were melted in 140 mM KCl, 10 mM $MgCl_2$, 20 mM HEPES-HCl (pH 7.2) on a Lambda 2 (Perkin Elmer) spectrophotometer with a PTP-6 automatic multicell temperature programmer. The melting temperatures of complexes (Tm) were determined from the derivative maxima.

Primer extension reactions

Primer extension reactions were performed as previously described by Lee, et al., [Biochemistry (1994) 33:6024—6030]. The final concentrations of template, primer and blocking ODNs were $5 \times 10^{-10}$M, $4 \times 10^{-8}$M and $10^{-9}$M, respectively. Primer extension was carried out for 15 min at 45° C., and the products were analyzed by denaturing gel electrophoresis as described in the reference.

In the absence of any blocking ODN, the primer extension reaction generated a high molecular weight product which ran as an unresolved band in the sequencing gel. Weak bands corresponding to pause sites or to spontaneous termination events were reproducibly observed in all reaction mixtures. Unmodified 16-mer and 32-mer ODNs, fully complementary to the target, failed to block primer extension. Also without activity were complementary 8-mer and 16-mer ODNs, each of which was 3'-linked to a $CDPI_3$ group. Only a fully complementary 16-mer ODN with a 5'-conjugated $CDPI_3$ group arrested primer extension by T7 DNA polymerase. A complementary 8-mer ODN with the same 5'modification generated only a trace amount of blocked product. Control ODNs confirmed that inhibition of primer extension required both a complementary ODN and a covalently linked MGB. Two singly-mismatched 16-mer ODNs, each with a 5'-linked $CDPI_3$ peptide, were much less inhibitory than the perfectly matched ODN-MGB conjugates. Addition of unmodified 16-mer ODN together with an equimolar amount of free $CDPI_3$ had no effect on primer extension, emphasizing the importance of the conjugation of the MGB to the ODN. When a 5' acridine moiety was conjugated to the fully complementary 16-mer ODN instead of the MGB, a loss of inhibitory activity was seen.

Cell culture crosslinking experiment

The ODN-MGB conjugate was complementary to nucleotides 815-864 of the template strand of the DQβ1 allele [Proc. Natl. Acad. Sci. USA (1983) 80:7313–7317]. The human BSM B-cells used here are homozygous for this allele and express it constitutively. Prior to adding the ODN, the BSM cells were grown in a 25 ml flask to a density of $4.5 \times 10^6$ cells per ml of media. For each treatment the cells from a 2 ml aliquot of culture were pelleted and resuspended in 200 ul of serum free media which contained 0, 1, 10 or 50 μM 50-mer chlorambucil-linked ODN (either with or without a 3' conjugated $CDPI_3$ group). Each sample was incubated for 3.5 hours at 37° C. with 5% $CO_2$ in a 48-well microtiter plate. The cells were then transferred to Eppendorf 0.5 ml centrifuge tubes, pelleted 5 min at 2,000 rpm, washed twice with 500 μl phosphate buffered saline (PBS) and deproteinized with Proteinase K/SDS overnight at 37° C. After phenol/chloroform extraction and Rnase A digestion the DNA was treated with 1M pyrrolidine at 90° C. for 30 min. Pyrrolidine was removed by ethanol precipitation, and the ligation-mediated ploymerase chain reaction (PCR) reaction was performed as described by Lee et al. [Biochemistry (1994) 33:6024–6030]. Amplified DNA was analyzed on a sequencing gel to visualize any sequence specific nicking that might have resulted from alkylation of the target by the chlorambucil-containing ODNs. Results showed cleavage at the nucleotide on the target adjacent to the crosslinker on the ODN, and that the $CDPI_3$-containing 50-mer was 10-fold more efficient than the same ODN without the MGB in sequence specifically alkylating the 0302 allele.

Complete media was prepared from the following components (the serum free media lacked HI-FCS):

500 ml RPMI 1640 with L-Glutamine (2 mM) (Gibco BRL Cat. No. 11875-036)

50 ml of HI-FCS (Gibco BRL Cat. No. 26140, heat inactivated 30 min at 55° C.)

5 ml of 100×Penn/Strep (Gibco BRL Cat. No. 15070-022)

5 ml of 200 mM L-Glutamine (Gibco BRL Cat. No. 25030-024)

ml of 100×Sodium Pyruvate (11 mg/ml; made from Gibco BRL Cat. No. 11840-030)

ml of 1M HEPES, pH 7.3 (Gibco BRL Cat. No. 15630-3)

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGTTATTTTT  GAAGATACGA  ATTTCUCCAG  AGACACAGCA  GGATTTGTCA          50
```

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TTTTTTTTT TTTTT                                   1 6

What is claimed is:

1. An oligonucleotide minor groove binder combination comprising an oligonucleotide having a plurality of nucleotide units, a 3'-end and a 5'-end, and a minor groove binder moiety attached to at least one of said nucleotides through a linking group which covalently binds the minor groove binder moiety to the oligonucleotide through no more than 15 atoms, wherein the minor groove binder moiety is a molecule having a molecular weight of approximately 150 to approximately 2000 Daltons that before attachment to said oligonucleotide binds in a non-intercalating manner into the minor groove of double stranded DNA, RNA or hybrids thereof with an association constant greater than approximately $10^3 M^{-1}$ and wherein the minor groove binder is attached through the linking group to a site of the oligonucleotide which is selected from the group consisting of the 5'-end of the oligonucleotide, the 3'-end of the oligonucleotide and a heterocyclic base in an intermediate position within said oligonucleotide.

2. An oligonucleotide minor groove binder combination in accordance with claim 1 wherein the minor groove binder moiety including the linking group has the formula selected from the group consisting of groups (a), (b), (c), (d) and (e):

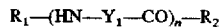      (a)

where $Y_1$ represents a 5-membered ring having two double bonds and 0 to 3 heteroatoms selected from the group consisting of N, S and O, the NH and CO groups are attached respectively to two ring carbons which are separated by one ring atom from one another, the ring atom positioned between said two ring carbons is substituted only with H when it is carbon or nitrogen and not substituted when it is oxygen or sulfur, each of the remaining ring atoms may be optionally substituted with 1, 2 or 3 $R_3$ groups;

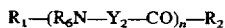      (b)

$Y_2$ is a ring system consisting of a 6-membered aromatic ring condensed with a 5-membered ring having one double bond, the condensed ring system having 0 to 3 heteroatoms selected from the group consisting of N, S and O, each of the $R_6N$ and CO groups is attached to a ring carbon which is in a different ring of the condensed ring system, and which is the second ring atom, respectively, from one common bridgehead ring atom, the CO and $NR_6$ groups thereby positioning 2 non-bridgehead ring atoms between themselves on one side and 3 non-bridgehead ring atoms on the other side of the condensed ring system, the two non-bridgehead ring atoms on the one side being optionally substituted with an $R_7$ group, the three non-bridgehead ring atoms on the other side of the condensed ring system being optionally substituted with an $R_3$ group;

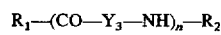      (c)

$Y_3$ is a 6-membered aromatic ring having 0 to 3N heteroatoms, and where each of the CO and NH groups is attached to a ring carbon, said ring carbons being in 1,4 position relative to one another, two ring atoms not occupied by the CO or NH groups on either one of the two sides of the 6-membered ring being optionally substituted with an $R_3$ group, the two ring atoms not occupied on the other side of the 6 membered ring being optionally substituted with an $R_7$ group;

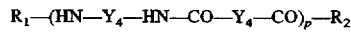      (d)

$Y_4$ is a 6-membered aromatic ring having 0 to 3N heteroatoms, and where each of the CO and NH groups is attached to a ring carbon, said ring carbons being in 1,4 position relative to one another in each ring, two ring atoms not occupied by the CO or NH groups on either one of the two sides of the 6-membered ring being optionally substituted with an $R_3$ group, the two ring atoms not occupied on the other side of the 6 membered ring being optionally substituted with an $R_7$ group;

      (e)

$Y_5$ is a ring system consisting of a 6-membered aromatic ring condensed with a 5-membered ring having one double bond, the condensed ring system having 0 to 3 heteroatoms selected from the group consisting of N, S and O, each of the $R_1$ and $R_2$ groups is attached to a ring carbon which is in a different ring of the condensed ring system, and which is the second ring atom, respectively, from one common bridgehead ring atom, the $R_1$ and $R_2$ groups thereby positioning 2 non-bridgehead ring atoms between themselves on one side and 3 non-bridgehead ring atoms on the other side of the condensed ring system, the two non-bridgehead ring atoms on the one side being optionally substituted with an $R_7$ group, the three non-bridgehead ring atoms on the other side of the condensed ring system being optionally substituted with an $R_3$ group;

where $R_1$ and $R_2$ independently are H, F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$, $R_4$, $H_2N(CH_2)_mCO$, $CONH_2$, $CONHR_4$ and $H_2N(CH_2)_mCOO(CH_2)_mS(CH_2)_m$ $C_6H_4NNC_6H_4$, $O(CH_2)_mCO$, $O(CH_2)_mCH(OH)$ $(CH_2)_mNHCO(CH_2)_mNH$, —O—, —S—, —HN $(CH_2)_mCO$, —CONH—, —CONR$_4$, —HN(CH$_2$)$_m$ $COO(CH_2)_mS(CH_2)_mC_6H_4NNC_6H_4$, and $-(CH_2)_mCH(OH)(CH_2)_mNHCO(CH_2)_mNH-$ or one of the $R_1$ and $R_2$ groups is absent;

$R_3$ is selected from the group consisting of F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$ and $R_4$, or the $R_3$ groups may form a 3, 4, 5 or 6 membered ring condensed to the $Y_1$ ring and substituted by one, two or three $R_4$;

$R_4$ is an alkyl or cycloalkyl group having 1 to 20 carbons, an alkenyl or cycloalkenyl group having 1 to 20 carbons and 1 to 3 double bonds, a carbocyclic aromatic group of no more than 25 carbons, a heterocyclic aromatic group of no more than 25 carbons, a carbocyclic or heterocyclic arylalkyl group of no more than 25 carbons, where $R_4$ may be optionally substituted with 1, 2 or 3 F, Cl, Br, I, $NH_2$, $NHR_5$, $N(R_5)_2$, $N(R_5)_3^+$, OH, $OR_5$, SH, $SR_5$, $COR_5$, $CONHR_5$, $CON(R_5)_2$ or $R_5$ groups;

$R_5$ is alkyl of 1 to 6 carbons, $R_6$ is H, alkyl of 1 to 5 carbons, or $R_6$ and $R_7$ jointly form a 4, 5, or 6 membered ring, optionally an —O—, —S—, —NH—, —NCH$_3$—, or N-lower alkyl group being part of said ring;

$R_7$ is F, methyl or ethyl; —CH$_2$—, or —CH$_2$CH$_2$—;

m is an integer between 1 to 10;

n is an integer between 1 to 10, and p is an integer between 1 to 5.

3. An oligonucleotide minor groove binder combination in accordance with claim 2 wherein the minor groove binding moiety including the linking group is represented by formula (a).

4. An oligonucleotide minor groove binder combination comprising an oligonucleotide having a plurality of nucleotide units, a 3'-end and a 5'-end, and a minor groove binder moiety attached to at least one of said nucleotides through a linking group which covalently binds the minor groove binder moiety to the oligonucleotide through no more than 15 atoms, wherein the minor groove binder moiety is a radical of a molecule having a molecular weight of approximately 150 to approximately 2000 Daltons that bind in a non-intercalating manner into the minor groove of double stranded DNA, RNA or hybdrids thereof with an association constant greater than approximately $10^3 M^{-1}$ wherein the minor groove binding moiety including the linking group is represented by formula (b)

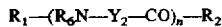  (b)

where $Y_2$ is a ring system consisting of a 6-membered aromatic ring condensed with a 5-membered ring having one double bond, the condensed ring system having 0 to 3 heteroatoms selected from the group consisting of N, S and O, each of the $R_6N$ and CO groups is attached to a ring carbon which is in a different ring of the condensed ring system, and which is the second ring atom, respectively, from one common bridgehead ring atom, the CO and $NR_6$ groups thereby positioning 2 non-bridgehead ring atoms between themselves on one side and 3 non-bridgehead ring atoms on the other side of the condensed ring system, the two non-bridgehead ring atoms on the one side being optionally substituted with an $R_7$ group, the three non-bridgehead ring atoms on the other side of the condensed ring system being optionally substituted with an $R_3$ group;

where $R_1$ and $R_2$ independently are H, F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$, $R_4$, $H_2N(CH_2)_mCO$, $CONH_2$, $CONHR_4$ and $H_2N(CH_2)_mCOO(CH_2)_mS(CH_2)_m C_6H_4NNC_6H_4$, $O(CH_2)_mCO$, $O(CH_2)_mCH(OH)$ $(CH_2)_mNHCO(CH_2)_mNH$, —O—, —S—, —HN$(CH_2)_mCO$, —CONH—, —CONR$_4$, —HN$(CH_2)_m$ $COO(CH_2)_mS(CH_2)_mC_6H_4NNC_6H_4$, and $-(CH_2)_mCH(OH)(CH_2)_mNHCO(CH_2)_mNH-$ or one of the $R_1$ and $R_2$ groups is absent;

$R_3$ is selected from the group consisting of F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$ and $R_4$;

$R_4$ is an alkyl or cycloalkyl group having 1 to 20 carbons, an alkenyl or cycloalkenyl group having 1 to 20 carbons and 1 to 3 double bonds, a carbocyclic aromatic group of no more than 25 carbons, a heterocyclic aromatic group of no more than 25 carbons, a carbocyclic or heterocyclic arylalkyl group of no more than 25 carbons, where $R_4$ may be optionally substituted with 1, 2 or 3 F, Cl, Br, I, $NH_2$, $NHR_5$, $N(R_5)_2$, $N(R_5)_3^+$, OH, $OR_5$, SH, $SR_5$, $COR_5$, $CONHR_5$, $CON(R_5)_2$ or $R_5$ groups;

$R_5$ is alkyl of 1 to 6 carbons, $R_6$ is H, alkyl of 1 to 5 carbons;

$R_7$ is F, methyl or ethyl; —CH$_2$—, or —CH$_2$CH$_2$—;

m is an integer between 1 to 10;

n is an integer between 1 to 10, and p is an integer between 1 to 5.

5. An oligonucleotide minor groove binder combination comprising an oligonucleotide having a plurality of nucleotide units, a 3'-end and a 5'-end, and a minor groove binder moiety attached to at least one of said nucleotides through a linking group which covalently binds the minor groove binder moiety to the oligonucleotide through no more than 15 atoms, wherein the minor groove binder moiety is a radical of a molecule having a molecular weight of approximately 150 to approximately 2000 Daltons that bind in a non-intercalating manner into the minor groove of double stranded DNA, RNA or hybdrids thereof with an association constant greater than approximately $10^3 M^{-1}$ wherein the minor groove binding moiety including the linking group is represented by formula (c)

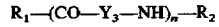  (c)

wherein $Y_3$ is a 6-membered aromatic ring having 0 to 3N heteroatoms, and where each of the CO and NH groups is attached to a ring carbon, said ring carbons being in 1,4 position relative to one another, two ring atoms not occupied by the CO or NH groups on either one of the two sides of the 6-membered ring being optionally substituted with an $R_3$ group, the two ring atoms not occupied on the other side of the 6 membered ring being optionally substituted with an $R_7$ group;

where $R_1$ and $R_2$ independently are H, F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$, $R_4$, $H_2N(CH_2)_mCO$, $CONH_2$, $CONHR_4$ and $H_2N(CH_2)_mCOO(CH_2)_mS(CH_2)_m C_6H_4NNC_6H_4$, $O(CH_2)_mCO$, $O(CH_2)_mCH(OH)$ $(CH_2)_mNHCO(CH_2)_mNH$, —O—, —S—, —HN $(CH_2)_mCO$, —CONH—, —CONR$_4$, —HN$(CH_2)_m$ $COO(CH_2)_mS(CH_2)_mC_6H_4NNC_6H_4$, and $-(CH_2)_mCH$ $(OH)(CH_2)_mNHCO(CH_2)_mNH-$ or one of the $R_1$ and $R_2$ groups is absent;

$R_3$ is selected from the group consisting of F, Cl, Br, I, $NH_2$, $NHR_4$, $N(R_4)_2$, $N(R_4)_3^+$, OH, $OR_4$, SH, $SR_4$, $COR_4$, $CONHR_4$, and $CON(R_4)_2$;

$R_4$ is an alkyl or cycloalkyl group having 1 to 20 carbons, an alkenyl or cycloalkenyl group having 1 to 20 car-

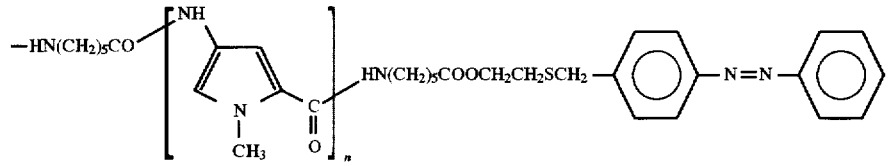

bons and 1 to 3 double bonds, a carbocyclic aromatic group of no more than 25 carbons, a heterocyclic aromatic group of no more than 25 carbons, a carbocyclic or heterocyclic arylalkyl group of no more than 25 carbons, where $R_4$ may be optionally substituted with 1, 2 or 3 F, Cl, Br, I, $NH_2$, $NHR_5$, $N(R_5)_2$, $N(R_5)_3^+$, OH, $OR_5$, SH, $SR_5$, $COR_5$, $CONHR_5$, $CON(R_5)_2$ or $R_5$ groups;

$R_5$ is alkyl of 1 to 6 carbons, $R_7$ is F, methyl or ethyl; —$CH_2$—, or —$CH_2CH_2$—;

m is an integer between 1 to 10, and n is an integer between 1 to 10.

6. An oligonucleotide minor groove binder combination in accordance with claim 1 wherein the minor groove binding moiety is attached to the 5'-end of the oligonucleotide.

7. An oligonucleotide minor groove binder combination in accordance with claim 1 wherein the minor groove binding moiety is attached to the 3'-end of the oligonucleotide.

8. An oligonucleotide minor groove binder combination in accordance with claim 1 wherein the minor groove binder moiety is attached to a nucleotide unit which is neither at the 3' nor at the 5' end of the oligonucleotide.

9. An oligonucleotide minor groove binder combination in accordance with claim 1 wherein the minor groove binder moiety is attached to the heterocyclic base portion of a nucleotide unit.

10. An oligonucleotide minor groove binder combination in accordance with claim 8 wherein the minor groove binder moiety is attached to the heterocyclic base portion of the nucleotide unit.

11. An oligonucleotide minor groove binder combination comprising an oligonucleotide having a plurality of nucleotide units, a 3'-end and a 5'-end, and a minor groove binder moiety attached to at least one of said nucleotides through a linking group which covalently binds the minor groove binder moiety to the oligonucleotide through no more than 15 atoms, wherein the minor groove binding moiety including the linking group has the formula where n is 2 to 5.

12. An oligonucleotide minor groove binder combination in accordance with claim 11 wherein the minor groove binding moiety is attached to the 3' end of the oligonucleotide.

13. An oligonucleotide minor groove binder combination comprising an oligonucleotide having a plurality of nucleotide units, a 3'-end and a 5'-end, and a minor groove binder moiety attached to at least one of said nucleotides through a linking group which covalently binds the minor groove binder moiety to the oligonucleotide through no more than 15 atoms, wherein the minor groove binding moiety including the linking group has the formula

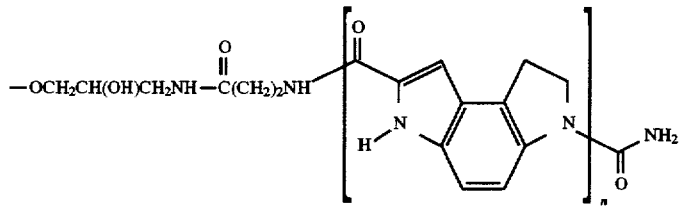

where n is 2 to 5.

14. An oligonucleotide minor groove binder combination in accordance with claim 13 wherein the minor groove binding moiety is attached to the 3' end of the oligonucleotide.

15. An oligonucleotide minor groove binder combination in accordance with claim 2 wherein the minor groove binding moiety is represented by formula (a) wherein the five membered ring has the structure

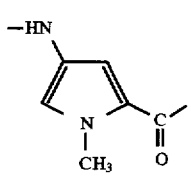

16. An oligonucleotide minor groove binder combination in accordance with claim 4 wherein the minor groove binding moiety is represented by formula (b) wherein the condensed ring system has the structure

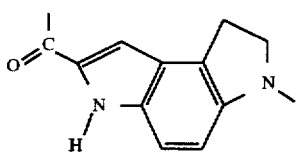

17. An oligonucleotide minor groove binder combination in accordance with claim 1 further comprising a cross-linking functionality covalently attached to at least one of said nucleotide units.

18. An oligonucleotide minor groove binder combination comprising an oligonucleotide having a plurality of nucleotide units, a 3'-end and a 5'-end, and a minor groove binder moiety attached to at least one of said nucleotides through a linking group which covalently binds the minor groove binder moiety to the oligonucleotide through no more than 15 atoms, the combination having the formula

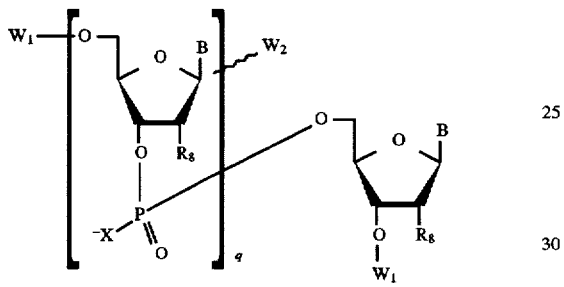

where x is O or S;

q is an integer between 3 to 100;

$R_8$ is H, OH, alkoxy having 1 to 6 carbons, O—$C_2$-$C_6$alkenyl, or F;

B is an aglycon selected from a group consisting of a heterocyclic base naturally found in nucleic acids and hypoxanthine, 2-aminoadenine, 2-thiouracil, 2-thiothymine, 5-$\underline{N}^4$-ethenocytosine, 4-aminopyrrazolo [3,4-d]pyrimidine, 6-amino-4-hydroxy-[3,4-d]pyrimidine;

$W_1$ is H, PO(OH)$_2$ or a salt thereof, or a minor groove binder moiety attached to the 3' or 5' end of said oligonucleotide, including the linking group which covalently binds the minor groove binder moiety to the oligonucleotide through no more than 15 atoms;

$W_2$ is absent or is a minor groove binder moiety attached to one of the aglycons B including the linking group which covalently binds the minor groove binder moiety to said aglycon, or $W_2$ is a cross-linking functionality including a linker arm which covalently binds the cross-linking functionality to said aglycon, wherein the minor groove binder moiety is a radical of a molecule having a molecular weight of approximately 150 to approximately 2000 Daltons that bind in a non-intercalating manner into the minor groove of double stranded DNA, RNA or hybdrids thereof with an association constant greater than approximately $M^{-1}$, with the proviso that at least one of said $W_1$ and $W_2$ groups is a minor groove binder moiety.

19. An oligonucleotide minor groove binder combination in accordance with claim 22 wherein the minor groove binder moiety including the linking group has the formula selected from the group consisting of groups (a), (b), (c), (d) and (e):

$$R_1—(HN—Y_1—CO)_n—R_2 \quad (a)$$

where $Y_1$ represents a 5-membered ring having two double bonds and 0 to 3 heteroatoms selected from the group consisting of N, S and O, the NH and CO groups are attached respectively to two ring carbons which are separated by one ring atom from one another, the ring atom positioned between said two ring carbons is substituted only with H when it is carbon or nitrogen and not substituted when it is oxygen or sulfur, each of the remaining ring atoms may be optionally substituted with 1, 2 or 3 $R_3$ groups;

$$R_1—(R_6N—Y_2—CO)_n—R_2 \quad (b)$$

where $Y_2$ is a ring system consisting of a 6-membered aromatic ring condensed with a 5-membered ring having one double bond, the condensed ring system having 0 to 3 heteroatoms selected from the group consisting of N, S and O, each of the $R_6N$ and CO groups is attached to a ring carbon which is in a different ring of the condensed ring system, and which is the second ring atom, respectively, from one common bridgehead ring atom, the CO and $NR_6$ groups thereby positioning 2 non-bridgehead ring atoms between themselves on one side and 3 non-bridgehead ring atoms on the other side of the condensed ring system, the two non-bridgehead ring atoms on the one side being optionally substituted with an $R_7$ group, the three non-bridgehead ring atoms on the other side of the condensed ring system being optionally substituted with an $R_3$ group;

$$R_1—(CO—Y_3—NH)_n—R_2 \quad (c)$$

$Y_3$ is a 6-membered aromatic ring having 0 to 3N heteroatoms, and where each of the CO and NH groups is attached to a ring carbon, said ring carbons being in 1,4 position relative to one another, two ring atoms not occupied by the CO or NH groups on either one of the two sides of the 6-membered ring being optionally substituted with an $R_3$ group, the two ring atoms not occupied on the other side of the 6 membered ring being optionally substituted with an $R_7$ group;

$$R_1—(HN—Y_4—HN—CO—Y_4—CO)_p—R_2 \quad (d)$$

where $Y_4$ is a 6-membered aromatic ring having 0 to 3N heteroatoms, and where each of the CO and NH groups is attached to a ring carbon, said ring carbons being in 1,4 position relative to one another in each ring, two ring atoms not occupied by the CO or NH groups on either one of the two sides of the 6-membered ring being optionally substituted with an $R_3$ group, the two ring atoms not occupied on the other side of the 6 membered ring being optionally substituted with an $R_7$ group;

$$R_1—(Y_5)_n—R_2 \quad (e)$$

where $Y_5$ is a ring system consisting of a 6-membered aromatic ring condensed with a 5-membered ring having one double bond, the condensed ring system having 0 to 3 heteroatoms selected from the group consisting of N, S and O, each of the $R_1$ and $R_2$ groups is attached to a ring carbon which is in a different ring of the condensed ring system, and which is the second ring atom, respectively, from one common bridgehead ring atom, the $R_1$ and $R_2$ groups thereby positioning 2 non-bridgehead ring atoms between themselves on one side and 3 non-bridgehead ring atoms on the other side of the condensed ring system, the two non-bridgehead ring atoms on the one side being optionally substituted with an $R_7$ group, the three non-bridgehead ring atoms on the other side of the condensed ring system being optionally substituted with an $R_3$ group;

where $R_1$ and $R_2$ independently are H, F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$, $R_4$, $H_2N(CH_2)_mCO$, $CONH_2$, $CONHR_4$ and $H_2N(CH_2)_mCOO(CH_2)_mS(CH_2)_m$ $C_6H_4NNC_6H_4$, —O—, —S—, —HN($CH_2)_mCO$, —CONH—, —$CONH_4$, —HN($CH_2)_mCOO(CH_2)_mS$ $(CH_2)_mC_6H_4NNC_6H_4$, and —($CH_2)_mCH(OH)(CH_2)_m$ $NHCO(CH_2)_mNH$— or one of the $R_1$ and $R_2$ groups is absent;

$R_3$ is selected from the group consisting of F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$ and $R_4$, or the $R_3$ groups may form a 3, 4, 5 or 6 membered ring condensed to the $Y_1$ rings;

$R_4$ is an alkyl or cycloalkyl group having 1 to 20 carbons, an alkenyl or cycloalkenyl group having 1 to 20 carbons and 1 to 3 double bonds, a carbocyclic aromatic group of no more than 25 carbons, a heterocyclic aromatic group of no more than 25 carbons, a carbocyclic or heterocyclic arylalkyl group of no more than 25 carbons, where $R_4$ may be optionally substituted with 1, 2 or 3 F, Cl, Br, I, $NH_2$, $NHR_5$, $N(R_5)_2$, $N(R_5)_3^+$, OH, $OR_5$, SH, $SR_5$, $COR_5$, $CONHR_5$, $CON(R_5)_2$ or $R_5$ groups;

$R_5$ is alkyl of 1 to 6 carbons, $R_6$ is H, alkyl of 1 to 5 carbons, or $R_6$ and $R_7$ jointly form a 4, 5, or 6 membered ring, optionally an —O—, —S—, —NH—, —$NCH_3$— or $\underline{N}$—lower alkyl group being part of said ring;

$R_7$ is F, methyl or ethyl; —$CH_2$—, or —$CH_2CH_2$—;

m is an integer between 1 to 10;

n is an integer between 1 to 10, and p is an integer between 1 to 5.

20. An oligonucleotide minor groove binder combination in accordance with claim 19 wherein at least one of the $W_1$ groups is a minor groove binder moiety and a linking group, and $W_2$ is absent.

21. An oligonucleotide minor groove binder combination in accordance with claim 19 wherein $W_2$ is a minor grove binder moiety and a linking group.

22. An oligonucleotide minor groove binder combination in accordance with claim 20 wherein the minor groove binding moiety including the linking group is represented by formula (a) wherein the five membered ring has the structure

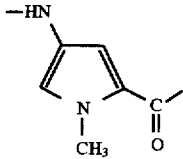

23. An oligonucleotide minor groove binder combination comprising an oligonucleotide having a plurality of nucleotide units, a 3'-end and a 5'-end, and a minor groove binder moiety attached to at least one of said nucleotides through a linking group which covalently binds the minor groove binder moiety to the oligonucleotide through no more than 15 atoms, wherein the minor groove binder moiety is a radical of a molecule having a molecular weight of approximately 150 to approximately 2000 Daltons that bind in a non-intercalating manner into the minor groove of double stranded DNA, RNA or hybdrids thereof with an association constant greater than approximately $10^3 M^{-1}$ wherein the minor groove binding moiety including the linking group is represented by formula (d)

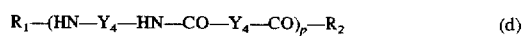

where $Y_4$ is a 6-membered aromatic ring having 0 to 3N heteroatoms, and where each of the CO and NH groups is attached to a ring carbon, said ring carbons being in 1,4 position relative to one another in each ring, two ring atoms not occupied by the CO or NH groups on either one of the two sides of the 6-membered ring being optionally substituted with an $R_3$ group, the two ring atoms not occupied on the other side of the 6 membered ring being optionally substituted with an $R_7$ group;

where $R_1$ and $R_2$ independently are H, F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$, $R_4$, $H_2N(CH_2)_mCO$, $CONH_2$, $CONHR_4$ and $H_2N(CH_2)_mCOO(CH_2)_mS(CH_2)_m$ $C_6H_4NNC_6H_4$, $O(CH_2)_mCO$, $O(CH_2)_mCH(OH)$ $(CH_2)_mNHCO(CH_2)_mNH$, —O—, —S—, —HN $(CH_2)_mCO$, —CONH—, —$CONR_4$, —HN($CH_2)_m$ $COO(CH_2)_mS(CH_2)_mC_6H_4NNC_6H_4$, and —($CH_2)_mCH$ $(OH)(CH_2)_mNHCO(CH_2)_mNH$— or one of the $R_1$ and $R_2$ groups is absent;

$R_3$ is selected from the group consisting of F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$ and $R_4$;

$R_4$ is an alkyl or cycloalkyl group having 1 to 20 carbons, an alkenyl or cycloalkenyl group having 1 to 20 carbons and 1 to 3 double bonds, a carbocyclic aromatic group of no more than 25 carbons, a heterocyclic aromatic group of no more than 25 carbons, a carbocyclic or heterocyclic arylalkyl group of no more than 25 carbons, where $R_4$ may be optionally substituted with 1, 2 or 3 F, Cl, Br, I, $NH_2$, $NHR_5$, $N(R_5)_2$, $N(R_5)_3^+$, OH, $OR_5$, SH, $SR_5$, $COR_5$, $CONHR_5$, $CON(R_5)_2$ or $R_5$ groups;

$R_5$ is alkyl of 1 to 6 carbons, $R_7$ is F, methyl or ethyl; —$CH_2$—, or —$CH_2CH_2$—;

m is an integer between 1 to 10, and p is an integer between 1 to 5.

24. An oligonucleotide minor groove binder combination comprising an oligonucleotide having a plurality of nucleotide units, a 3'-end and a 5'-end, and a minor groove binder moiety attached to at least one of said nucleotides through a linking group which covalently binds the minor groove binder moiety to the oligonucleotide through no more than 15 atoms, wherein the minor groove binder moiety is a radical of a molecule having a molecular weight of approximately 150 to approximately 2000 Daltons that bind in a non-intercalating manner into the minor groove of double stranded DNA, RNA or hybdrids thereof with an association constant greater than approximately $10^3 M^{-1}$ wherein the minor groove binding moiety including the linking group is represented by formula (e)

63

$Y_5$ is a ring system consisting of a 6-membered aromatic ring condensed with a 5-membered ring having one double bond, the condensed ring system having 0 to 3 heteroatoms selected from the group consisting of N, S and O, each of the $R_1$ and $R_2$ groups is attached to a ring carbon which is in a different ring of the condensed ring system, and which is the second ring atom, respectively, from one common bridgehead ring atom, the $R_1$ and $R_2$ groups thereby positioning 2 non-bridgehead ring atoms between themselves on one side and 3 non-bridgehead ring atoms on the other side of the condensed ring system, the two non-bridgehead ring atoms on the one side being optionally substituted with an $R_7$ group, the three non-bridgehead ring atoms on the other side of the condensed ring system being optionally substituted with an $R_3$ group;

where $R_1$ and $R_2$ independently are H, F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$, $R_4$, $H_2N(CH_2)_mCO$, $CONH_2$, $CONHR_4$ and $H_2N(CH_2)_mCOO(CH_2)_mS(CH_2)_mC_6H_4NNC_6H_4$, $O(CH_2)_mCO$, $O(CH_2)_mCH(OH)(CH_2)_mNHCO(CH_2)_mNH$, —O—, —S—, —HN$(CH_2)_mCO$, —CONH—, —CONR_4$, —HN(CH_2)_m$COO(CH_2)_mS(CH_2)_mC_6H_4NNC_6H_4$, and —$(CH_2)_mCH(OH)(CH_2)_mNHCO(CH_2)_mNH$— or one of the $R_1$ and $R_2$ groups is absent;

$R_3$ is selected from the group consisting of F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$ and $R_4$, or the $R_3$ groups may form a 3, 4, 5 or 6 membered ring condensed to the $Y_5$ ring and substituted by one, two or three $R_4$;

$R_4$ is an alkyl or cycloalkyl group having 1 to 20 carbons, an alkenyl or cycloalkenyl group having 1 to 20 carbons and 1 to 3 double bonds, a carbocyclic aromatic group of no more than 25 carbons, a heterocyclic aromatic group of no more than 25 carbons, a carbocyclic or heterocyclic arylalkyl group of no more than 25 carbons, where $R_4$ may be optionally substituted with 1, 2 or 3 F, Cl, Br, I, $NH_2$, $NHR_5$, $N(R_5)_2$, $N(R_5)_3^+$, OH, $OR_5$, SH, $SR_5$, $COR_5$, $CONHR_5$, $CON(R_5)_2$ or $R_5$ groups;

$R_5$ is alkyl of 1 to 6 carbons, $R_7$ is F, methyl or ethyl; —$CH_2$—, or —$CH_2CH_2$—;

m is an integer between 1 to 10, and n is an integer between 1 to 10.

25. An oligonucleotide minor groove binder combination comprising an oligonucleotide having a plurality of nucleotide units, a 3'-end and a 5'-end, and a minor groove binder moiety attached to at least one of said nucleotides through a linking group which covalently binds the minor groove binder moiety to the oligonucleotide through no more than 15 atoms, wherein the minor groove binding moiety including the linking group has the formula

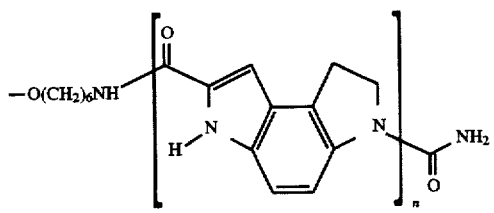

where n is 2 to 5.

26. An oligonucleotide minor groove binder combination comprising an oligonucleotide having a plurality of nucleotide units, a 3'-end and a 5'-end, and

64 a minor groove binder moiety attached to at least one of said nucleotides through a linking group which covalently binds the minor groove binder moiety to the oligonucleotide through no more than 15 atoms, wherein the minor groove binding moiety including the linking group is represented by formula (a)

$$R_1—(HN—Y_1—CO)_n—R_2 \qquad (a)$$

wherein HN—$Y_1$—CO has the structure,

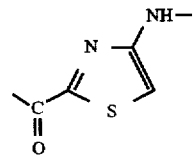

and $R_1$ and $R_2$ independently are H, F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$, $R_4$, $H_2N(CH_2)_mCO$, $CONH_2$, $CONHR_4$ and $H_2N(CH_2)_mCOO(CH_2)_mS(CH_2)_mC_6H_4NNC_6H_4$, $O(CH_2)_mCO$, $O(CH_2)_mCH(OH)(CH_2)_mNHCO(CH_2)_mNH$, —O—, —S—, —HN$(CH_2)_mCO$, —CONH—, —CONR_4$, —HN$(CH_2)_mCOO(CH_2)_mS(CH_2)_mC_6H_4NNC_6H_4$, and —$(CH_2)_mCH(OH)(CH_2)_mNHCO(CH_2)_mNH$— or one of the $R_1$ and $R_2$ groups is absent;

$R_4$ is an alkyl or cycloalkyl group having 1 to 20 carbons, an alkenyl or cycloalkenyl group having 1 to 20 carbons and 1 to 3 double bonds, a carbocyclic aromatic group of no more than 25 carbons, a heterocyclic aromatic group of no more than 25 carbons, a carbocyclic or heterocyclic arylalkyl group of no more than 25 carbons, where $R_4$ may be optionally substituted with 1, 2 or 3 F, Cl, Br, I, $NH_2$, $NHR_5$, $N(R_5)_2$, $N(R_5)_3^+$, OH, $OR_5$, SH, $SR_5$, $COR_5$, $CONHR_5$, $CON(R_5)_2$ or $R_5$ groups;

$R_5$ is alkyl of 1 to 6 carbons, m is an integer between 1 to 10, and n is an integer between 1 to 10.

27. An oligonucleotide minor groove binder combination comprising an oligonucleotide having a plurality of nucleotide units, a 3'-end and a 5'-end, and a minor groove binder moiety attached to at least one of said nucleotides through a linking group which covalently binds the minor groove binder moiety to the oligonucleotide through no more than 15 atoms, the combination having the formula

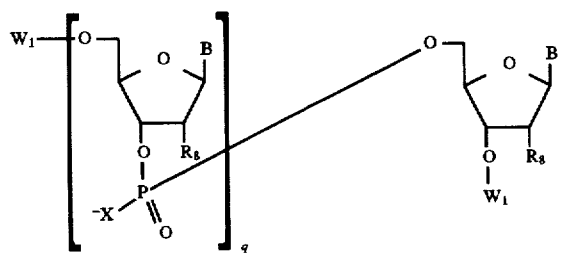

where X is O or S;

q is an integer between 3 to 100;

$R_8$ is H, OH, alkoxy having 1 to 6 carbons, O—$C_2$-$C_6$alkenyl, or F;

B is an aglycon selected from a group consisting of a heterocyclic base naturally found in nucleic acids and hypoxanthine, 2-aminoadenine, 2-thiouracil, 2-thiothymine, 5-$N^4$-ethenocytosine, 4-aminopyrazolo [3,4-d]pyrimidine, 6-amino-4-hydroxypyrazolo-[3,4-d] pyrimidine;

$W_1$ is H, $PO(OH)_2$ or a salt thereof, or a minor groove binder moiety attached to the 3' or 5' end of said oligonucleotide, including the linking group which covalently binds the minor groove binder moiety to the oligonucleotide through no more than 15 atoms, with the proviso that at least one of the $W_1$ groups is a minor group binder and a linking group and wherein the minor groove binding moiety including the linking group is represented by formula (a)

(a)

wherein HN—$Y_1$—CO has the structure,

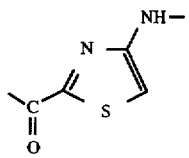

and $R_1$ and $R_2$ independently are H, F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$, $R_4$, $H_2N(CH_2)_mCO$, $CONH_2$, $CONHR_4$ and $H_2N(CH_2)_mCOO(CH_2)_mS(CH_2)_mC_6H_4NNC_6H_4$, $O(CH_2)_m$ CO, $O(CH_2)_mCH(OH)(CH_2)_mNHCO(CH_2)_mNH$, —O—, —S—, —HN($CH_2)_mCO$, —CONH—, —$CONR_4$, —HN $(CH_2)_mCOO(CH_2)_mS(CH_2)_mC_6H_4NNC_6H_4$, and —$(CH_2)_m$ $CH(OH)(CH_2)_mNHCO(CH_2)_mNH$— or one of the $R_1$ and $R_2$ groups is absent;

$R_4$ is an alkyl or cycloalkyl group having 1 to 20 carbons, an alkenyl or cycloalkenyl group having 1 to 20 carbons and 1 to 3 double bonds, a carbocyclic aromatic group of no more than 25 carbons, a heterocyclic aromatic group of no more than 25 carbons, a carbocyclic or heterocyclic arylalkyl group of no more than 25 carbons, where $R_4$ may be optionally substituted with 1, 2 or 3 F, Cl, Br, I, $NH_2$, $NHR_5$, $N(R_5)_2$, $N(R_5)_3^+$, OH, $OR_5$, SH, $SR_5$, $COR_5$, $CONHR_5$, $CON(R_5)_2$ or $R_5$ groups;

$R_5$ is alkyl of 1 to 6 carbons, m is an integer between 1 to 10, and n is an integer between 1 to 10.

28. An oligonucleotide minor groove binder combination comprising an oligonucleotide having a plurality of nucleotide units, a 3'-end and a 5'-end, and a minor groove binder moiety attached to at least one of said nucleotides through a linking group which covalently binds the minor groove binder moiety to the oligonucleotide through no more than 15 atoms, the combination having the formula

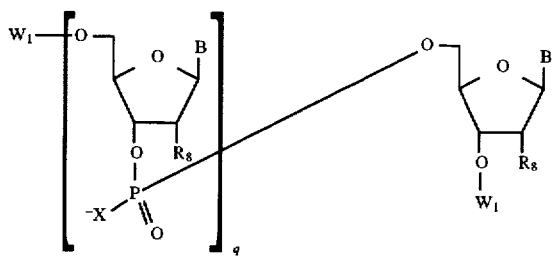

where X is O or S;

q is an integer between 3 to 100;

$R_8$ is H, OH, alkoxy having 1 to 6 carbons, O—$C_2$-$C_6$alkenyl, or F;

B is an aglycon selected from a group consisting of a heterocyclic base naturally found in nucleic acids and hypoxanthine, 2-aminoadenine, 2-thiouracil, 2-thiothymine, 5-$N^4$-ethenocytosine, 4-aminopyrrazolo [3,4-d]pyrimidine, 6-amino-4-hydroxypyrazolo-[3,4-d]pyrimidine;

$W_1$ is H, $PO(OH)_2$ or a salt thereof, or a minor groove binder moiety attached to the 3' or 5' end of said oligonucleotide, including the linking group which covalently binds the minor groove binder moiety to the oligonucleotide through no more than 15 atoms, with the proviso that at least one of the $W_1$ groups is a minor groove binder and a linking group and wherein the minor groove binding moiety including the linking group is represented by the formula

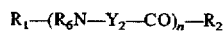

(b)

wherein $R_6N$—$Y_2$—CO has the formula

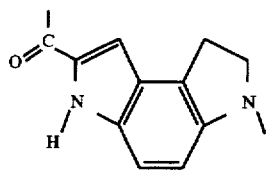

and $R_1$ and $R_2$ independently are H, F, Cl, Br, I, $NH_2$, $NHR_4$, $N(R_4)_2$, $N(R_4)_3^+$, OH, $OR_4$, SH, $SR_4$, $COR_4$, $CONHR_4$, $CON(R_4)_2$, $R_4$, $H_2N(CH_2)_mCO$, $CONH_2$, $CONHR_4$ and $H_2N(CH_2)_mCOO(CH_2)_mS(CH_2)_mC_6H_4NNC_6H_4$, $O(CH_2)_m$ CO, $O(CH_2)_mCH(OH)(CH_2)_mNHCO(CH_2)_mNH$, —O—, —S—, —HN($CH_2)_mCO$, —CONH—, —$CONR_4$, —HN $(CH_2)_mCOO(CH_2)_mS(CH_2)_mC_6H_4NNC_6H_4$, and —$(CH_2)_m$ $CH(OH)(CH_2)_mNHCO(CH_2)_mNH$— or one of the $R_1$ and $R_2$ groups is absent;

$R_4$ is an alkyl or cycloalkyl group having 1 to 20 carbons, an alkenyl or cycloalkenyl group having 1 to 20 carbons and 1 to 3 double bonds, a carbocyclic aromatic group of no more than 25 carbons, a heterocyclic aromatic group of no more than 25 carbons, a carbocyclic or heterocyclic arylalkyl group of no more than 25 carbons, where $R_4$ may be optionally substituted with 1, 2 or 3 F, Cl, Br, I, $NH_2$, $NHR_5$, $N(R_5)_2$, $N(R_5)_3^+$, OH, $OR_5$, SH, $SR_5$, $COR_5$, $CONHR_5$, $CON(R_5)_2$ or $R_5$ groups;

$R_5$ is alkyl of 1 to 6 carbons, m is an integer between 1 to 10, and n is an integer between 1 to 10.

* * * * *